(12) United States Patent
Frederick et al.

(10) Patent No.: US 11,406,458 B2
(45) Date of Patent: Aug. 9, 2022

(54) ROBOTIC DEVICE WITH COMPACT JOINT DESIGN AND RELATED SYSTEMS AND METHODS

(71) Applicant: Board of Regents of the University of Nebraska, Lincoln, NE (US)

(72) Inventors: Tom Frederick, Lincoln, NE (US); Eric Markvicka, Brush, CO (US); Shane Farritor, Lincoln, NE (US); Dmitry Oleynikov, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 68 days.

(21) Appl. No.: 16/538,902

(22) Filed: Aug. 13, 2019

(65) Prior Publication Data

US 2019/0388166 A1 Dec. 26, 2019

Related U.S. Application Data

(63) Continuation of application No. 14/938,667, filed on Nov. 11, 2015, now Pat. No. 10,376,322.
(Continued)

(51) Int. Cl.
*A61B 34/30* (2016.01)
*A61B 18/14* (2006.01)
(Continued)

(52) U.S. Cl.
CPC .............. *A61B 34/30* (2016.02); *A61B 18/14* (2013.01); *B25J 9/0087* (2013.01); *B25J 9/046* (2013.01);
(Continued)

(58) Field of Classification Search
CPC ....... A61B 34/30; A61B 18/14; A61B 18/082; A61B 18/1445; A61B 2034/305;
(Continued)

(56) References Cited

U.S. PATENT DOCUMENTS 3,870,264 A 3/1975 Robinson
3,989,952 A 11/1976 Timberlake et al.
(Continued)

FOREIGN PATENT DOCUMENTS

CN 102821918 12/2012
DE 102010040405 3/2012
(Continued)

OTHER PUBLICATIONS

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
(Continued)

*Primary Examiner* — Thomas A Giuliani
*Assistant Examiner* — Catherine Premraj
(74) *Attorney, Agent, or Firm* — Sean D. Solberg

(57) ABSTRACT

The embodiments disclosed herein relate to various robotic and/or in vivo medical devices having compact joint configurations. Other embodiments relate to various medical device components, including forearms having grasper or cautery end effectors, that can be incorporated into certain robotic and/or in vivo medical devices.

19 Claims, 17 Drawing Sheets

Related U.S. Application Data

(60) Provisional application No. 62/078,192, filed on Nov. 11, 2014.

(51) Int. Cl.
*B25J 9/00* (2006.01)
*B25J 9/10* (2006.01)
*B25J 9/04* (2006.01)
*A61B 18/12* (2006.01)
*A61B 18/08* (2006.01)
*A61B 17/00* (2006.01)
*A61B 18/00* (2006.01)

(52) U.S. Cl.
CPC ............ *B25J 9/102* (2013.01); *A61B 18/082* (2013.01); *A61B 18/1445* (2013.01); *A61B 2017/00398* (2013.01); *A61B 2017/00407* (2013.01); *A61B 2017/00477* (2013.01); *A61B 2018/00595* (2013.01); *A61B 2018/1253* (2013.01); *A61B 2018/1422* (2013.01); *A61B 2034/305* (2016.02); *A61B 2217/005* (2013.01); *A61B 2217/007* (2013.01); *A61B 2218/002* (2013.01); *A61B 2218/007* (2013.01)

(58) Field of Classification Search
CPC ........... A61B 2017/00398; A61B 2017/00407; A61B 2017/00477; A61B 2018/00595; A61B 2018/1253; A61B 2018/1422; A61B 2217/005; A61B 2217/007; A61B 2218/002; A61B 2218/007; B25J 9/0087; B25J 9/046; B25J 9/102
See application file for complete search history.

(56) References Cited

U.S. PATENT DOCUMENTS

| | | |
|---|---|---|
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyaki |
| 4,736,645 A | 4/1988 | Zimmer |
| 4,771,652 A | 9/1988 | Zimmer |
| 4,852,391 A | 8/1989 | Ruch |
| 4,896,015 A | 1/1990 | Taboada et al. |
| 4,922,755 A | 5/1990 | Oshiro et al. |
| 4,922,782 A * | 5/1990 | Kawai .................. B25J 9/0084 29/402.08 |
| 4,990,050 A | 2/1991 | Tsuge et al. |
| 5,019,968 A | 5/1991 | Wang et al. |
| 5,172,639 A | 12/1992 | Wiesman et al. |
| 5,195,388 A | 3/1993 | Zona et al. |
| 5,201,325 A | 4/1993 | McEwen et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,441,494 A | 1/1995 | Oritz |
| 5,388,528 A | 2/1995 | Pelrine et al. |
| 5,436,542 A | 7/1995 | Petelin et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyaman et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,086,529 A | 7/2000 | Arndt |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minor et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tiemey et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |

(56) References Cited

U.S. PATENT DOCUMENTS

| | | |
|---|---|---|
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,497,651 B1 | 12/2002 | Kan et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |

(56) References Cited

U.S. PATENT DOCUMENTS

| | | |
|---|---|---|
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,231,610 B2 | 7/2012 | Jo et al. |
| 8,353,897 B2 | 1/2013 | Doyle et al. |
| 9,089,353 B2 | 7/2015 | Farritor et al. |
| 9,649,020 B2 | 5/2017 | Finlay |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zando-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0229338 A1 | 12/2003 | Irion et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0234435 A1 | 10/2005 | Layer |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0100501 A1 | 5/2006 | Berkelman et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0135803 A1 | 6/2007 | Belson |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |

(56) References Cited

U.S. PATENT DOCUMENTS

| | | | |
|---|---|---|---|
| 2008/0269557 A1 | 10/2008 | Marescaux et al. | |
| 2008/0269562 A1 | 10/2008 | Marescaux et al. | |
| 2009/0020724 A1 | 1/2009 | Paffrath | |
| 2009/0024142 A1 | 1/2009 | Ruiz Morales | |
| 2009/0048612 A1 | 2/2009 | Farritor et al. | |
| 2009/0054909 A1 | 2/2009 | Farritor et al. | |
| 2009/0069821 A1 | 3/2009 | Farritor et al. | |
| 2009/0076536 A1 | 3/2009 | Rentschler et al. | |
| 2009/0137952 A1 | 5/2009 | Ramamurthy et al. | |
| 2009/0143787 A9 | 6/2009 | De La Pena | |
| 2009/0163929 A1 | 6/2009 | Yeung et al. | |
| 2009/0171373 A1 | 7/2009 | Farritor et al. | |
| 2009/0234369 A1 | 9/2009 | Bax et al. | |
| 2009/0236400 A1 | 9/2009 | Cole et al. | |
| 2009/0240246 A1 | 9/2009 | Devill et al. | |
| 2009/0247821 A1 | 10/2009 | Rogers | |
| 2009/0248038 A1 | 10/2009 | Blumenkranz et al. | |
| 2009/0281377 A1 | 11/2009 | Newell et al. | |
| 2009/0305210 A1 | 12/2009 | Guru et al. | |
| 2010/0010294 A1 | 1/2010 | Conlon et al. | |
| 2010/0016659 A1 | 1/2010 | Weitzner et al. | |
| 2010/0016853 A1 | 1/2010 | Burbank | |
| 2010/0042097 A1 | 2/2010 | Newton et al. | |
| 2010/0056863 A1 | 3/2010 | Dejima et al. | |
| 2010/0069710 A1 | 3/2010 | Yamatani et al. | |
| 2010/0069940 A1 | 3/2010 | Miller et al. | |
| 2010/0081875 A1 | 4/2010 | Fowler et al. | |
| 2010/0139436 A1 | 6/2010 | Kawashima et al. | |
| 2010/0185212 A1 | 7/2010 | Sholev | |
| 2010/0198231 A1 | 8/2010 | Manzo et al. | |
| 2010/0245549 A1 | 9/2010 | Allen et al. | |
| 2010/0262162 A1 | 10/2010 | Omori | |
| 2010/0292691 A1 | 11/2010 | Brogna | |
| 2010/0318059 A1 | 12/2010 | Farritor et al. | |
| 2011/0020779 A1 | 1/2011 | Hannaford et al. | |
| 2011/0071347 A1 | 3/2011 | Rogers et al. | |
| 2011/0071544 A1 | 3/2011 | Steger et al. | |
| 2011/0098529 A1 | 4/2011 | Ostrovsky et al. | |
| 2011/0224605 A1 | 9/2011 | Farritor et al. | |
| 2011/0230894 A1 | 9/2011 | Simaan et al. | |
| 2011/0237890 A1 | 9/2011 | Farritor et al. | |
| 2011/0238080 A1 | 9/2011 | Ranjit et al. | |
| 2011/0264078 A1 | 10/2011 | Lipow et al. | |
| 2011/0270443 A1 | 11/2011 | Kamiya et al. | |
| 2012/0029727 A1 | 2/2012 | Sholev | |
| 2012/0035582 A1 | 2/2012 | Nelson et al. | |
| 2012/0109150 A1 | 5/2012 | Quaid et al. | |
| 2012/0116362 A1 | 5/2012 | Kieturakis | |
| 2012/0179168 A1 | 7/2012 | Farritor et al. | |
| 2012/0253515 A1 | 10/2012 | Coste-Maniere et al. | |
| 2013/0131695 A1* | 5/2013 | Scarfogliero | A61B 34/30 606/130 |
| 2013/0345717 A1 | 12/2013 | Markvicka et al. | |
| 2014/0039515 A1 | 2/2014 | Mondry et al. | |
| 2014/0046340 A1 | 2/2014 | Wilson et al. | |
| 2014/0058205 A1 | 2/2014 | Frederick et al. | |
| 2014/0303434 A1 | 10/2014 | Farritor et al. | |
| 2015/0051446 A1 | 2/2015 | Farritor et al. | |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| JP | 05-115425 | 5/1993 |
| JP | 2006508049 | 9/1994 |
| JP | 07-016235 | 1/1995 |
| JP | 07-136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2003220065 | 8/2003 |
| JP | 2004144533 | 5/2004 |
| JP | 2004-180781 | 7/2004 |
| JP | 2004322310 | 11/2004 |
| JP | 2004329292 | 11/2004 |
| JP | 2006507809 | 3/2006 |
| JP | 2009106606 | 5/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| JP | 6268293 B2 | 1/2018 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 1/2006 |
| WO | 2006079108 | 7/2006 |
| WO | 2007011654 | 1/2007 |
| WO | 2007111571 | 10/2007 |
| WO | 2007149559 | 12/2007 |
| WO | 2009023851 | 2/2009 |
| WO | 2009144729 | 12/2009 |
| WO | 2010050771 | 5/2010 |
| WO | 2011075693 | 6/2011 |
| WO | 2011118646 | 9/2011 |
| WO | 2011135503 | 11/2011 |
| WO | 2013009887 | 1/2013 |
| WO | 2014011238 | 1/2014 |
| WO | 2015088655 A1 | 6/2015 |

OTHER PUBLICATIONS

Ollendorf et al., "Postoperative Immune Function Varies Inversely with the Degree of Surgical Trauma in a Murine Model," Surgical Endoscopy 1997; 11:427-430.

Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.

Atmel 80C5X2 Core, http://www.atmel.com, 2006, 186pp.

Bailey et al., "Complications of Laparoscopic Surgery," Quality Medical Publishers, Inc., 1995, 25pp.

Ballantyne, "Robotic Surgery, Telerobotic Surgery, Telepresence, and Telementoring," Surgical Endoscopy, 2002; 16: 1389-1402.

Bauer et al., "Case Report: Remote Percutaneous Renal Percutaneous Renal Access Using a New Automated Telesurgical Robotic System," Telemedicine Journal and e-Health 2001; (4): 341-347.

Begos et al., "Laparoscopic Cholecystectomy: From Gimmick to Gold Standard," J Clin Gastroenterol, 1994; 19(4): 325-330.

Berg et al., "Surgery with Cooperative Robots," Medicine Meets Virtual Reality, Feb. 2007, 1 pg.

Breda et al., "Future developments and perspectives in laparoscopy," Eur. Urology 2001; 40(1): 84-91.

Breedveld et al., "Design of Steerable Endoscopes to Improve the Visual Perception of Depth During Laparoscopic Surgery," ASME, Jan. 2004; vol. 126, pp. 1-5.

Breedveld et al., "Locomotion through the Intestine by means of Rolling Stents," Proceedings of the ASME Design Engineering Technical Conferences, 2004, pp. 1-7.

Calafiore et al., Multiple Arterial Conduits Without Cardiopulmonary Bypass: Early Angiographic Results,: Ann Thorac Surg, 1999; 67: 450-456.

Camarillo et al., "Robotic Technology in Surgery: Past, Present and Future," The American Journal of Surgery, 2004; 188: 2S-15.

Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.

(56) References Cited

OTHER PUBLICATIONS

Dumpert et al., "Stereoscopic In Vivo Surgical Robots," IEEE Sensors Special Issue on In Vivo Sensors for Medicine, Jan. 2007, 10 pp.
Green, "Telepresence Surgery", Jan. 1, 1995, Publisher: IEEE Engineering in Medicine and Biology.
Cleary et al., "State of the Art in Surgical Rooties: Clinical Applications and Technology Challenges", "Computer Aided Surgery", Jan. 1, 2002, pp. 312-328, vol. 6.
Stoianovici et al., "Robotic Tools for Minimally Invasive Urologic Surgery", Jan. 1, 2002, pp. 1-17.
Franzino, "The Laprotek Surgical System and the Next Generation of Robotics," Surg Clin North Am, 2003 83(6): 1317-1320.
Franklin et al.,"Prospective Comparison of Open vs. Laparoscopic Colon Surgery for Carcinoma: Five-Year Results," Dis Colon Rectum, 1996; 39: S35-S46.
Flynn et al., "Tomorrow's surgery: micromotors and microrobots for minimally invasive procedures," Minimally Invasive Surgery & Allied Technologies, 1998; 7(4): 343-352.
Fireman et al., "Diagnosing small bowel Crohn's desease with wireless capsule endoscopy," Gut 2003; 52: 390-392.
Fearing et al., "Wing Transmission for a Micromechanical Flying Insect," Proceedings of the 2000 IEEE International Conference to Robotics & Automation, Apr. 2000; 1509-1516.
Faraz el al., "Engineering Approaches to Mechanical and Robotic Design for Minimaly Invasive Surgery (MIS)," Kluwer Academic Publishers (Boston), 2000, 13pp.
Falcone et al., "Robotic Surgery," Clin. Obstet. Gynecol. 2003, 46(1): 37-13.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Dumpert et al., "Improving in Vivo Robot Visioin Quality," from the Proceedings of Medicine Meets Virtual Realtiy, Long Beach, CA, Jan. 26-29, 2005. 1 pg.
Dakin et al., "Comparison of laparoscopic skills performance between standard instruments and two surgical robotic systems," Surg Endosc., 2003; 17: 574-579.
Cuschieri, "Technology for Minimal Access Surgery," BMJ, 1999, 319: 1-6.
Grady, "Doctors Try New Surgery for Gallbladder Removal," The New York Times, Apr. 20, 2007, 3 pp.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Chanthasopeephan et al., (2003), "Measuring Forces in Liver Cutting: New Equipment and Experimenal Results," Annals of Biomedical Engineering 31: 1372-1382.
Cavusoglu et al.,"Robotics for Telesurgery: Second Generation Berkeley/UCSF Laparoscopic Telesurgical Workstation and Looking Towards the Future Applications," Industrial Robot: An International Journal, 2003; 30(1): 22-29.
Guber et al., "Miniaturized Instrument Systems for Minimally Invasive Diagnosis and Therapy," Biomedizinische Technic. 2002, Band 47, Erganmngsband 1: 198-201.

\* cited by examiner

ROBOTIC DEVICE WITH COMPACT JOINT DESIGN AND RELATED SYSTEMS AND METHODS

CROSS-REFERENCE TO RELATED APPLICATION(S)

This application claims priority as a continuation of U.S. patent application Ser. No. 14/938,667, filed Nov. 11, 2015, and entitled "Robotic Device with Compact Joint Design and Related Systems and Methods," which issued as U.S. Pat. No. 10,376,322 on Aug. 13, 2019; which claims the benefit under 35 U.S.C. § 119(e) to U.S. Provisional Application 62/078,192, filed Nov. 11, 2014 and entitled "Robotic Device with Compact Joint Design and Related Systems and Methods," both of which are hereby incorporated herein by reference in their entireties.

GOVERNMENT SUPPORT

This invention was made with government support under Grant No. W81XWH-08-02-0043, awarded by the U.S. Army Medical Research and Materiel Command; Grant No. W81XWH-09-2-0185, awarded by the U.S. Army Medical Research and Materiel Command; Grant No. DGE1041000, awarded by the National Science Foundation; and Grant Nos. NNX09A071A and NNX10AJ26G, awarded by the National Aeronautics and Space Administration. The government has certain rights in the invention.

FIELD OF THE INVENTION

The embodiments disclosed herein relate to various medical devices and related components, including robotic and/or in vivo medical devices and related components, such as arms and end effectors. More specifically, certain embodiments include various robotic medical devices, including robotic devices that are disposed within a body cavity and/or disposed through an orifice or opening in the body cavity. Additional embodiments relate to various robotic device arms and/or medical device operational components, often referred to as "end effectors." Certain arm and/or end effector embodiments disclosed herein relate to forearms having grasper and/or cautery end effectors. Further embodiments relate to methods of operating the above devices and operational components.

BACKGROUND OF THE INVENTION

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices, including improved robotic arms and end effectors for use with the devices.

BRIEF SUMMARY OF THE INVENTION

Discussed herein are various robotic devices having a compact body design that results from the configuration of the internal components. Also discussed herein are various arms and/or end effectors that can be used with the robotic devices disclosed herein or other known robotic devices.

In Example 1, a robotic device comprises an elongate device body, a first shoulder joint, and a first arm operably coupled to the first shoulder joint. The elongate body comprises a first lower gear drivetrain and a first upper gear drivetrain. The first lower gear drivetrain comprises a first motor and a first driveshaft operably coupled to the first motor and to a first lower bevel gear, wherein the first driveshaft is rotatably disposed within and is concentric with the first lower bevel gear and a first upper bevel gear. The first upper gear drivetrain comprises a second motor operably coupled to the first upper bevel gear. The first shoulder joint comprises a first output shaft operably coupled to a first output bevel gear, wherein the first output bevel gear is operably coupled to the first upper and first lower bevel gears.

Example 2 relates to the robotic device according to Example 1, wherein the first arm is a first upper arm, wherein the device further comprises a first forearm operably coupled to the first upper arm.

Example 3 relates to the robotic device according to Example 2, further comprising a first end effector operably coupled to the first forearm.

Example 4 relates to the robotic device according to Example 1, further comprising a second lower gear drivetrain, a second upper gear drivetrain, a second shoulder joint, and a second arm operably coupled to the second shoulder joint. The second lower gear drivetrain comprises a third motor and a second driveshaft operably coupled to the third motor and to a second lower bevel gear, wherein the second driveshaft is rotatably disposed within and is concentric with the second lower bevel gear and a second upper bevel gear. The second upper gear drivetrain comprises a fourth motor operably coupled to the second upper bevel gear. The second shoulder joint comprising a second output shaft operably coupled to a second output bevel gear, wherein the second output bevel gear is operably coupled to the second upper and second lower bevel gears.

Example 5 relates to the robotic device according to Example 4, wherein the second arm is a second upper arm, wherein the device further comprises a second forearm operably coupled to the second upper arm.

Example 6 relates to the robotic device according to Example 5, further comprising a second end effector operably coupled to the second forearm.

In Example 7, a robotic device comprises an elongate device body, a first shoulder joint, and a first arm operably coupled to the first shoulder joint. The elongate device body comprises a first shoulder gear set, a first lower gear drivetrain, and a first upper gear drivetrain. The first shoulder gear set comprises a first upper bevel gear, a first lower bevel gear, and a first output bevel gear operably coupled to the upper and lower bevel gears. The first lower gear drivetrain comprises a first motor and a first driveshaft operably coupled to the first motor and to the first lower bevel gear, wherein the first driveshaft is rotatably disposed within and is concentric with the first upper and lower bevel gears. The first upper gear drivetrain comprises a second motor operably coupled to the first upper bevel gear. The first shoulder joint comprises a first output shaft operably coupled to the first output bevel gear.

Example 8 relates to the robotic device according to Example 7, wherein the first arm is a first upper arm, wherein the device further comprises a first forearm operably coupled to the first upper arm.

Example 9 relates to the robotic device according to Example 8, wherein further comprising a first end effector operably coupled to the first forearm.

Example 10 relates to the robotic device according to Example 7, further comprising a second shoulder gear set, a second lower gear drivetrain, a second upper gear drivetrain, a second shoulder joint, and a second arm operably coupled to the second shoulder joint. The second shoulder gear set comprises a second upper bevel gear, a second lower bevel gear, and a second output bevel gear operably coupled to the second upper and second lower bevel gears. The second lower gear drivetrain comprises a third motor and a second driveshaft operably coupled to the third motor and to the second lower bevel gear, wherein the second driveshaft is rotatably disposed within and is concentric with the second upper and second lower bevel gears. The second upper gear drivetrain comprises a fourth motor operably coupled to the second upper bevel gear. The second shoulder joint comprises a second output shaft operably coupled to the second output bevel gear.

Example 11 relates to the robotic device according to Example 10, wherein the second arm is a second upper arm, wherein the device further comprises a second forearm operably coupled to the second upper arm.

Example 12 relates to the robotic device according to Example 11, further comprising a second end effector operably coupled to the second forearm.

In Example 13, an arm for a robotic device comprises an arm body, a slideable sleeve associated with the arm body, a cautery shaft disposed within the slideable sleeve, a cautery hook disposed at the distal end of the cautery shaft, a rotation actuation component operably coupled to the cautery shaft, and a sleeve actuation component operably coupled to the slideable sleeve. Actuation of the rotation actuation component causes the cautery shaft to rotate. Actuation of the sleeve actuation component causes the slideable sleeve to move between a retracted position and an extended position.

Example 14 relates to the arm according to Example 13, wherein the cautery shaft comprises a proximal cautery shaft and a distal cautery shaft, wherein the proximal cautery shaft is operably coupled to the distal cautery shaft.

Example 15 relates to the arm according to Example 13, further comprising a first drive gear coupled to the rotation actuation component and a first driven gear coupled to cautery shaft. The first drive gear and the first driven gear are rotationally coupled such that rotation of the rotation actuation component causes rotation of the cautery shaft.

Example 16 relates to the arm according to Example 13, further comprising a second drive gear coupled to the sleeve actuation component, and a second driven gear coupled to a leadscrew, wherein the leadscrew is disposed within and threadably coupled to a nut, wherein the nut is coupled to the slideable sheath. The second drive gear and the second driven gear are rotationally coupled such that rotation of the sleeve actuation component causes rotation of the leadscrew, which causes the nut to move laterally, which causes the slideable sheath to move between the retracted position and the extended position.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1:
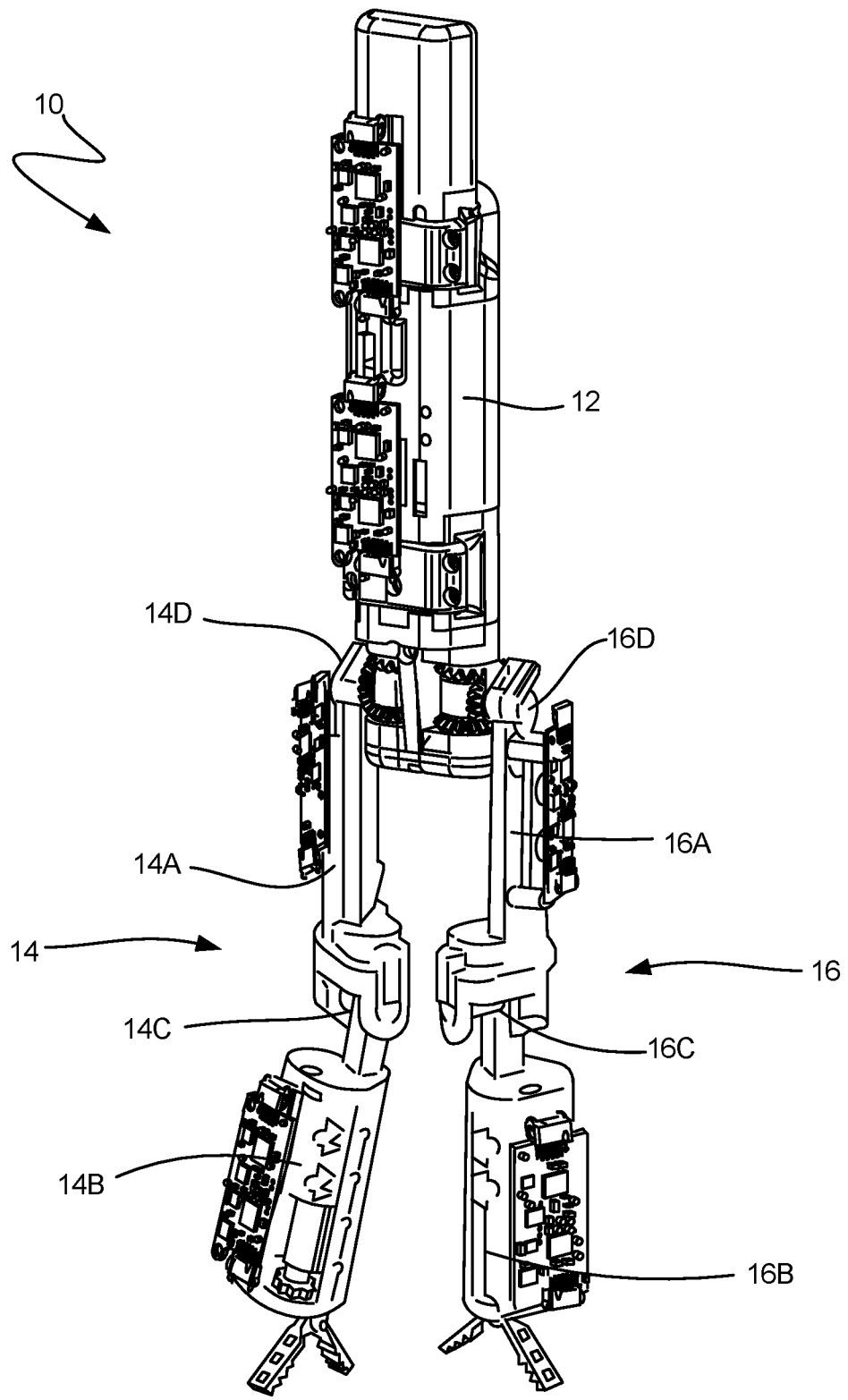
FIG. 1 is a perspective view of a robotic device, according to one embodiment.

The various embodiments disclosed or contemplated herein relate to surgical robotic devices, systems, and methods. More specifically, various embodiments relate to various medical devices, including robotic devices and related methods and systems. Certain implementations relate to such devices for use in laparo-endoscopic single-site (LESS) surgical procedures. Further embodiments relate to certain robotic arms and/or end effectors that can used with the robotic devices, including grasper and/or cautery end effectors.

It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in copending U.S. applications Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), 61/030,588 (filed on Feb. 22, 2008), Ser. No. 12/171,413 (filed on Jul. 11, 2008 and entitled "Methods and Systems of Actuation in Robotic Devices"), Ser. No. 12/192,663 (filed Aug. 15, 2008 and entitled Medical Inflation, Attachment, and Delivery Devices and Related Methods"), Ser. No. 12/192,779 (filed on Aug. 15, 2008 and entitled "Modular and Cooperative Medical Devices and Related Systems and Methods"), Ser. No. 12/324,364 (filed Nov. 26, 2008 and entitled "Multifunctional Operational Component for Robotic Devices"), 61/640,879 (filed on May 1, 2012), Ser. No. 13/493,725 (filed Jun. 11, 2012 and entitled "Methods, Systems, and Devices Relating to Surgical End Effectors"), Ser. No. 13/546,831 (filed Jul. 11, 2012 and entitled "Robotic Surgical Devices, Systems, and Related Methods"), 61/680,809 (filed Aug. 8, 2012), Ser. No. 13/573,849 (filed Oct. 9, 2012 and entitled "Robotic Surgical Devices, Systems, and Related Methods"), and Ser. No. 13/738,706 (filed Jan. 10, 2013 and entitled "Methods, Systems, and Devices for Surgical Access and Insertion"), and U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), all of which are hereby incorporated herein by reference in their entireties.

Certain device and system implementations disclosed in the applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

An exemplary embodiment of a robotic device 10 is depicted in FIG. 1. The device 10 has a main body 12, a right arm 14, and a left arm 16. Each of the right 14 and left 16 arms is comprised of two segments or links. That is, the right arm 14 has an upper arm (or first link) 14A and a forearm (or second link) 14B, and the left arm 16 has an upper arm (or first link) 16A and a forearm (or second link) 16B. In each arm 14, 16, the forearm 14B, 16B is coupled to the upper arm 14A, 16A at an elbow joint (or first joint) 14C, 16C, and the upper arm 14A, 16A is coupled to the main body 12 at a shoulder joint (or second joint) 14D, 16D.

Figure 2A:
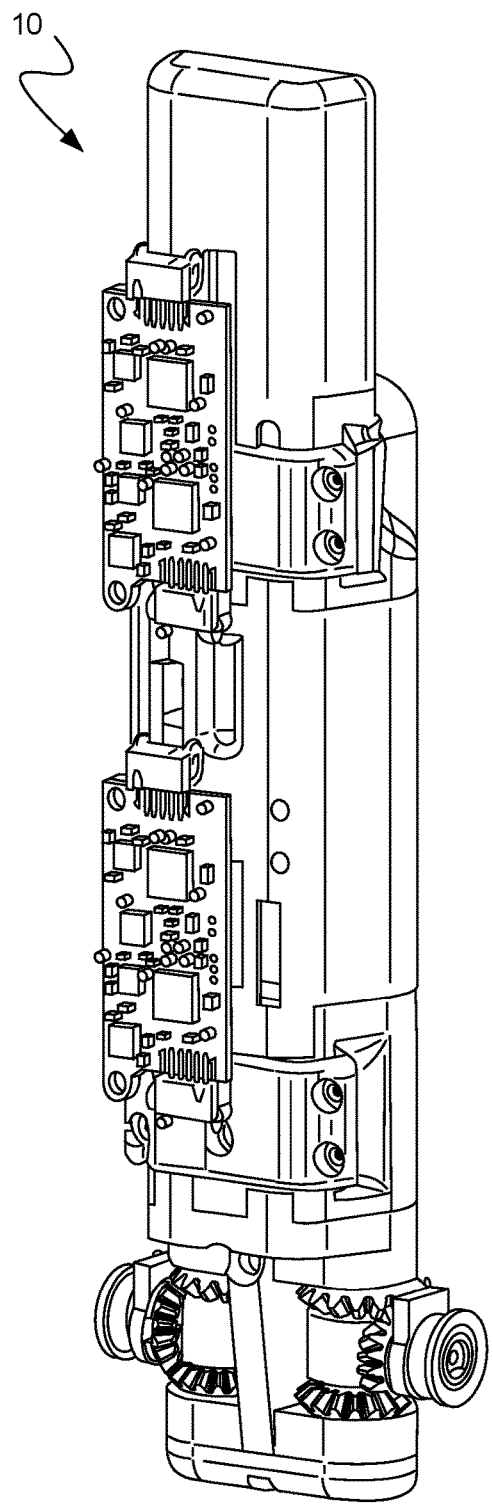
FIG. 2A is a perspective view of the device body of the robotic device of FIG. 1, according to one embodiment.
Figure 2B:
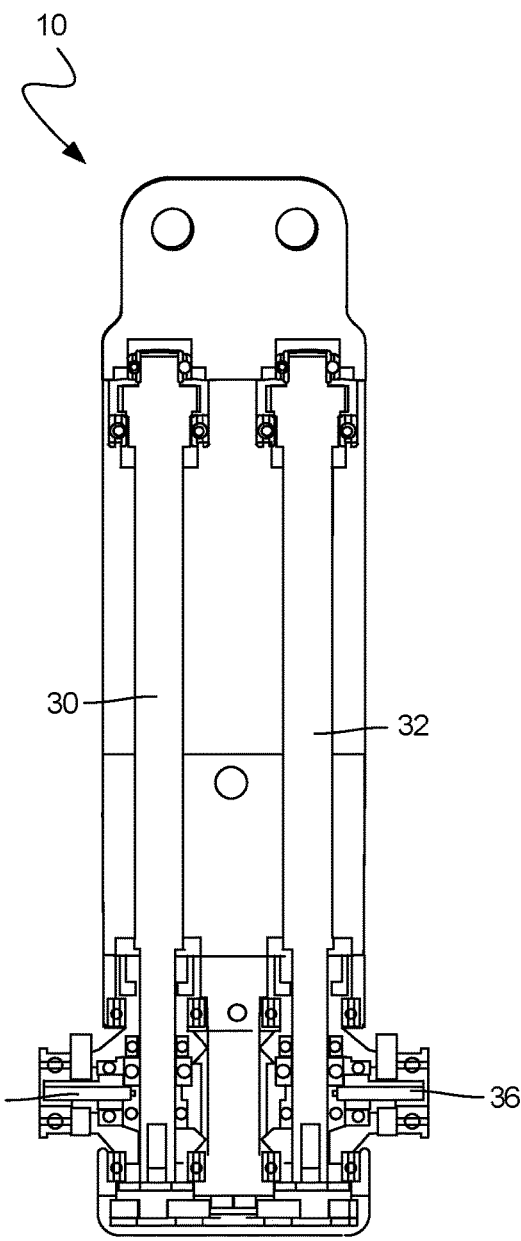
FIG. 2B is a cross-sectional front view of the device body of the robotic device of FIG. 1, according to one embodiment.

FIGS. 2A and 2B depict the device body 10, according to one exemplary embodiment. More specifically, FIG. 2A depicts a perspective view of the body 10, while FIG. 2B depicts a cross-sectional front view of the body 10 in which certain internal components of the body 10 are visible. The body 10 has a right driveshaft 30 and a left driveshaft 32, both of which are rotatably disposed within the body 10. A right output shaft 34 and a left output shaft 36 are operably coupled to the right driveshaft 30 and the left driveshaft 32, respectively. More specifically, as discussed in further detail below, the right driveshaft 30 is coupled to a right lower bevel gear 72 such that the rotation of the driveshaft 30 causes the rotation of the right lower bevel gear 72. In the remainder of this description of the body 10 and its components, the description will focus on the right side of the body 10, the right shoulder 14D, and the right forearm 14A. It is understood that the components of the left side of the body 10, the left shoulder 16D, and the left forearm 16A, the relationship of those components to each other, and their functionality is substantially similar to those components of the right side of the body 10, the right shoulder 14D, and the right forearm 14A.

Figure 3A:
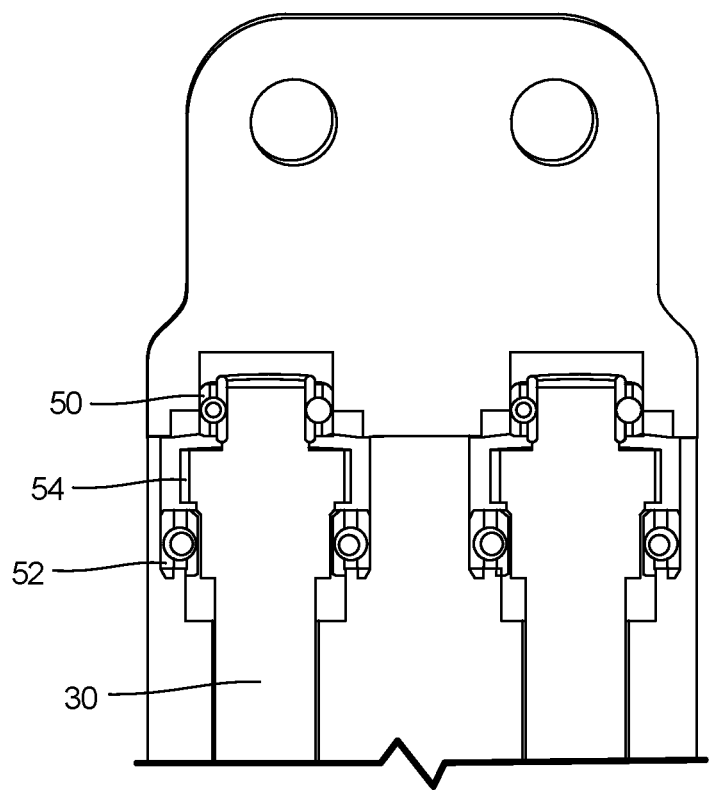
FIG. 3A is a cross-sectional front view of a portion of the device body of the robotic device of FIG. 1, according to one embodiment.
Figure 3B:
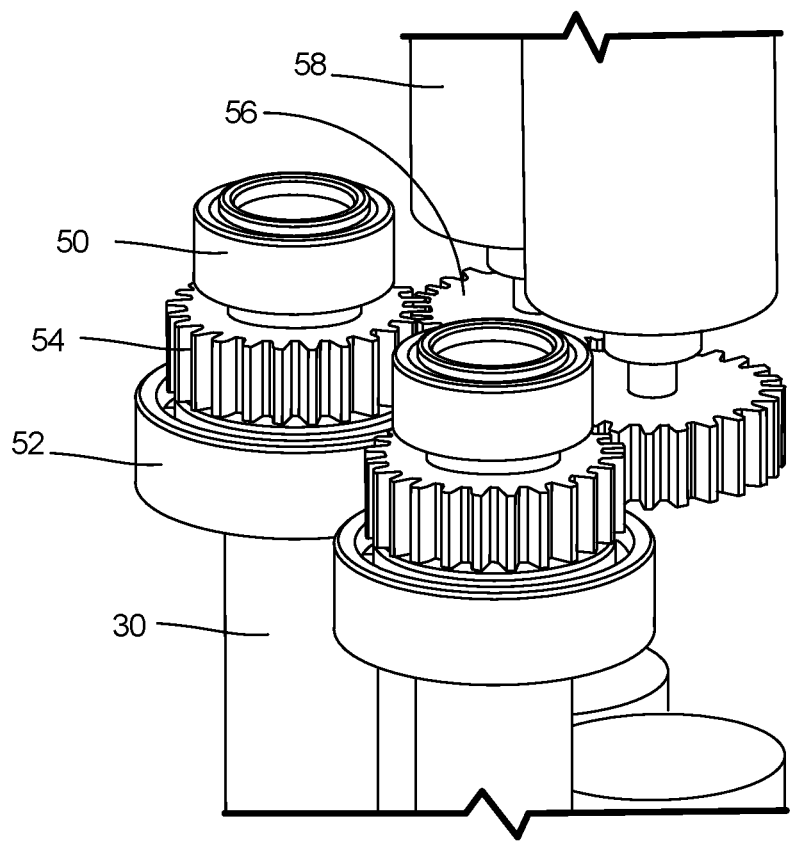
FIG. 3B is a perspective view of certain internal components of the device body of the robotic device of FIG. 1, according to one embodiment.

One implementation of an expanded view of the proximal end of the body 10 is depicted in FIGS. 3A and 3B. As shown, the proximal end of the right driveshaft 30 is rotatably supported in the body 10 via a first bearing 50 and a second bearing 52. The driveshaft 30 has a driven gear 54 defined along its length such that the driven gear 54 is disposed between the two bearings 50, 52. As best shown in FIG. 3B, the driven gear 54 is coupled to a drive gear 56, which is operably coupled to a motor 58. Actuation of the motor 58 causes the rotation of the drive gear 56, which causes the rotation of the driven gear 54, which causes the rotation of the driveshaft 30.

Figure 4A:
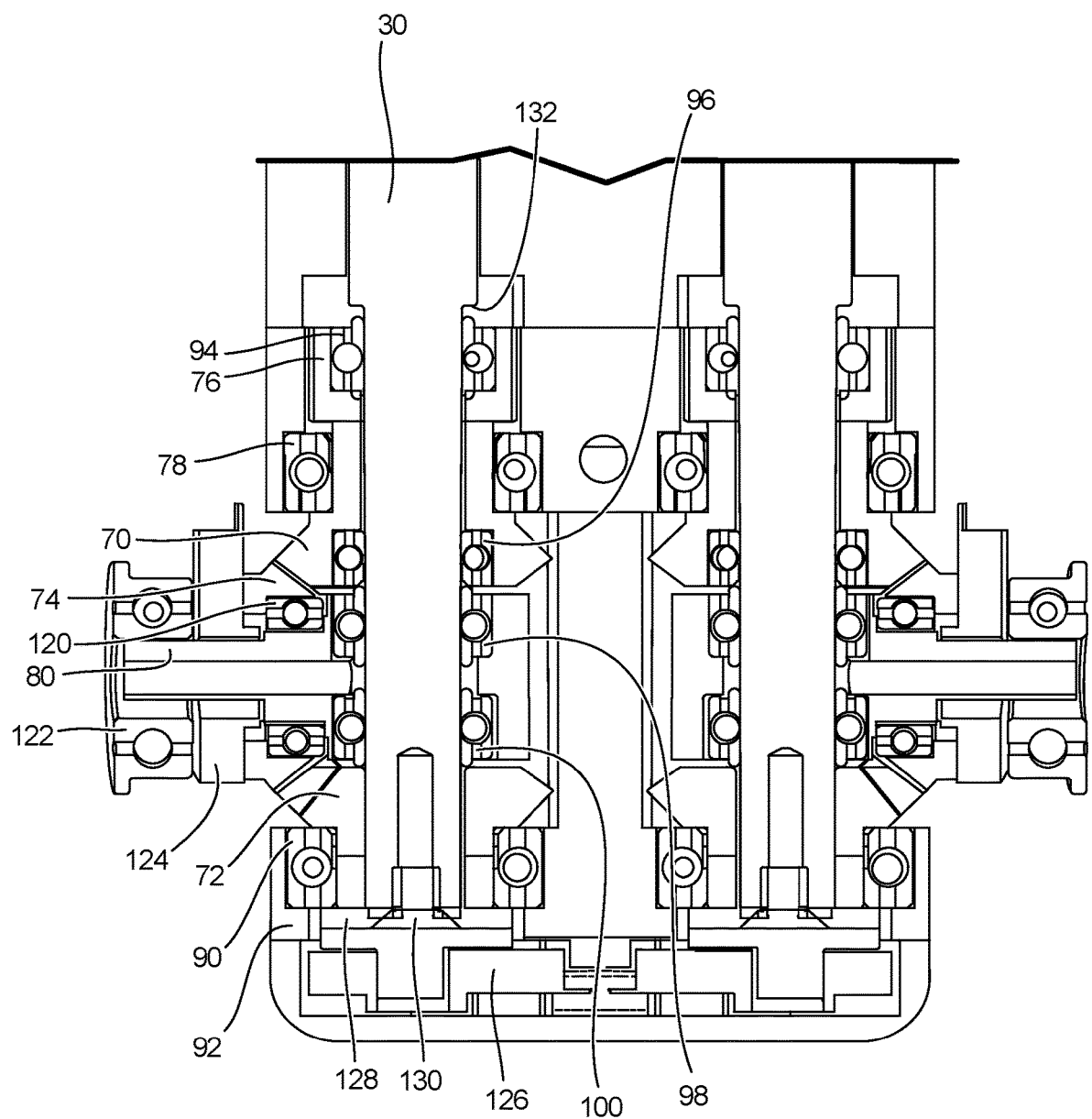
FIG. 4A is a cross-sectional front view of a portion of the device body of the robotic device of FIG. 1, according to one embodiment.
Figure 4B:
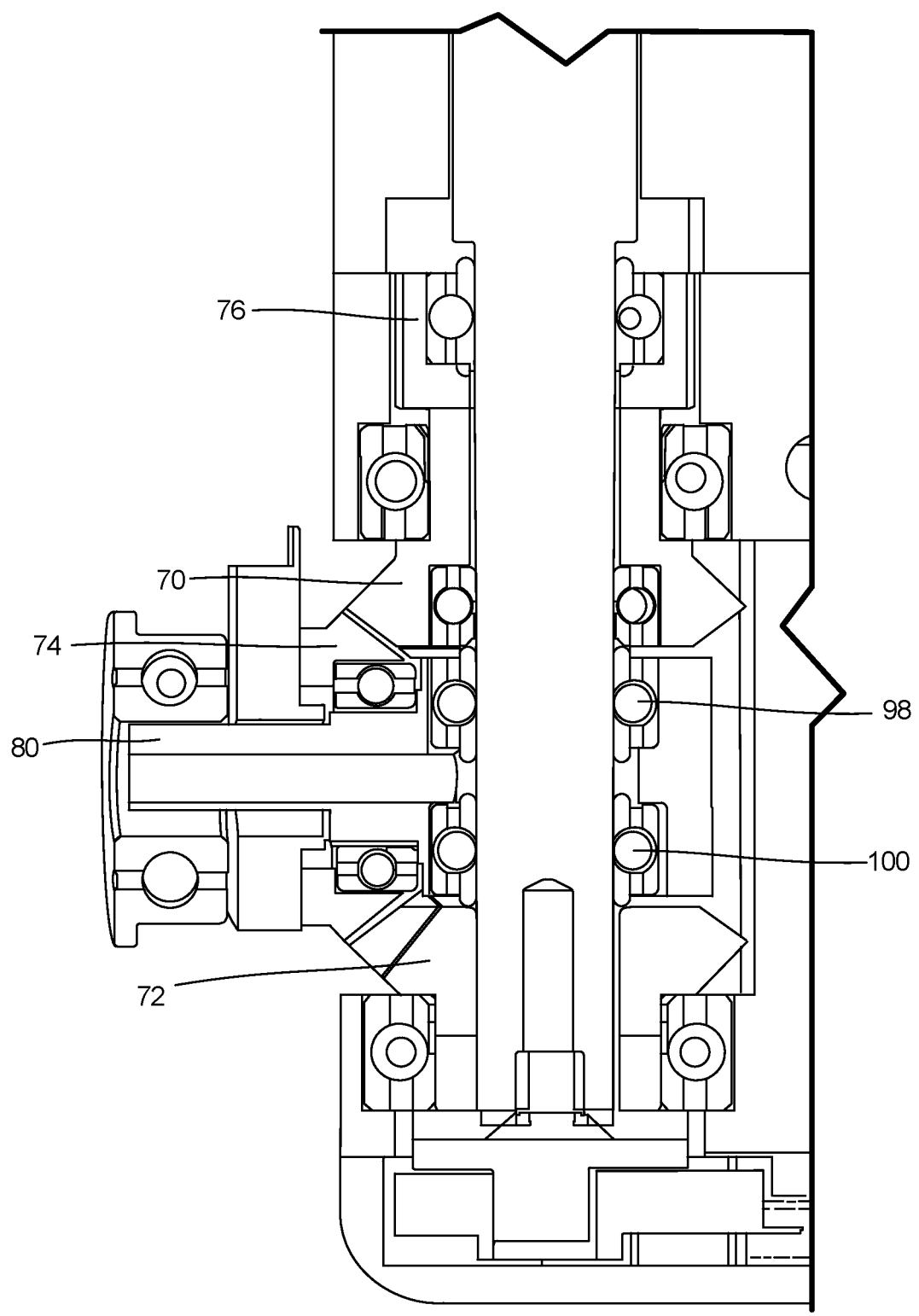
FIG. 4B is a cross-sectional front view of a portion of the device body of the robotic device of FIG. 1, according to one embodiment.
Figure 4C:
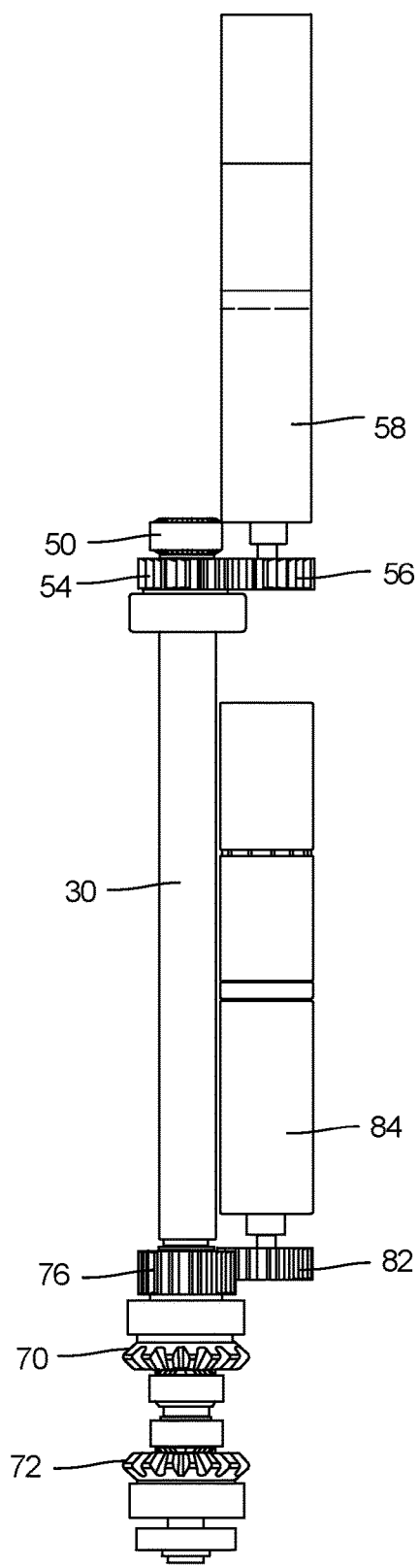
FIG. 4C is a side view of certain internal components of the device body of the robotic device of FIG. 1, according to one embodiment.

Further views of the internal components of the body 10 are shown in FIGS. 4A, 4B, 4C, and 4D, in accordance with one embodiment. As best shown in FIGS. 4A and 4B, there are three right bevel gears in the distal portion of the body 10: the right upper bevel gear 70, the right lower bevel gear 72, and the right output bevel gear 74, all of which are positioned around the output shaft 80 and are rotatably coupled to each other. The upper bevel gear 70 is coupled (or "rotationally constrained") to a driven gear 76 such that rotation of the driven gear 76 causes rotation of the upper bevel gear 70, and both the upper bevel gear 70 and the driven gear 76 are supported by upper bevel gear bearing 78. As best shown in FIG. 4C, the driven gear 76 is coupled to a drive gear 82, which is coupled to a motor 84. Actuation of the motor 84 ultimately causes rotation of the upper bevel gear 70.

The lower bevel gear 72 is coupled (or rotationally constrained) to the driveshaft 30. Thus, as best shown in FIG. 4C, the motor 58 actuates rotation of the drive gear 56, which causes rotation of the driven gear 54, which causes rotation of the driveshaft 30, which causes rotation of the lower bevel gear 72 (as also shown in FIGS. 4A and 4B). The lower bevel gear 72 is supported by lower bevel gear bearing 90, which is inset into the right lower bevel gear support 92.

As best shown in FIGS. 4A and 4B, the distal portion of the driveshaft 30 is supported by bearing 94 (which is inset into driven gear 76), bearing 96 (which is inset into upper bevel gear 70), and bearings 98, 100 (which are inset into output shaft 80).

Figure 7A:
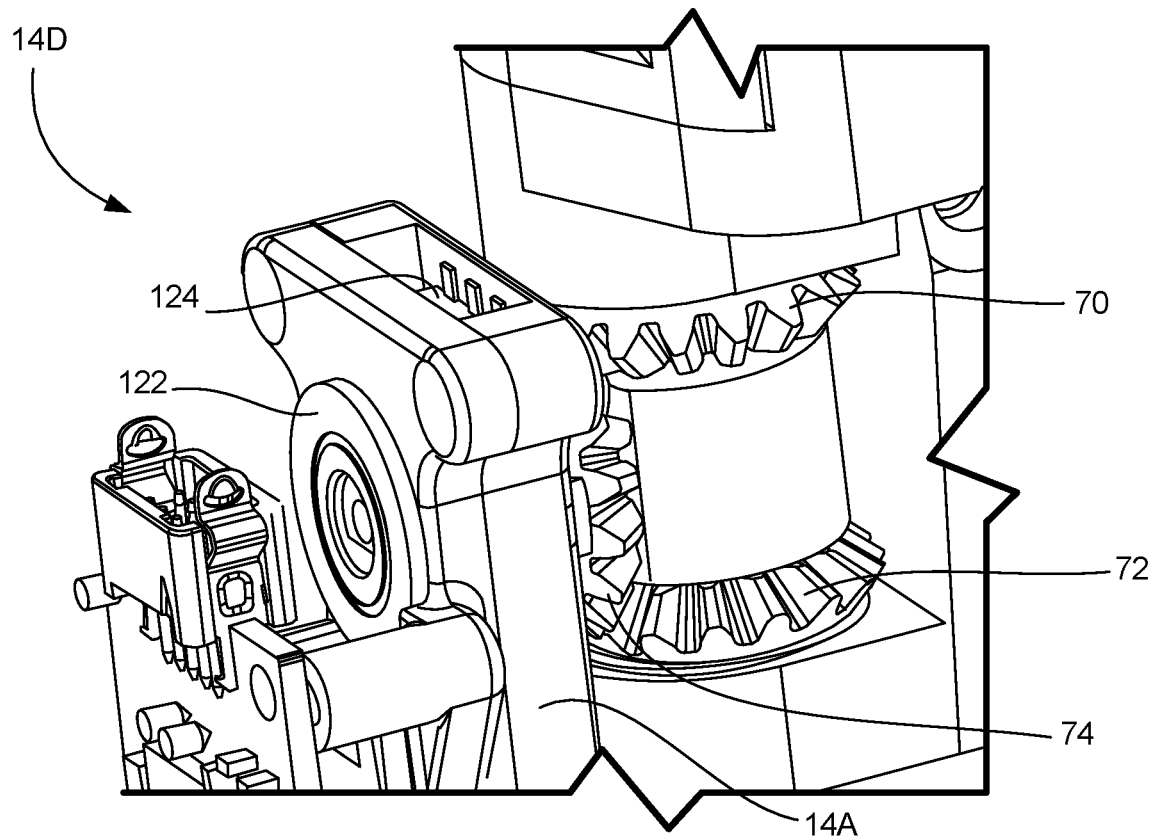
FIG. 7A is a perspective view of a right shoulder joint of a robotic device, according to one embodiment.
Figure 8A:
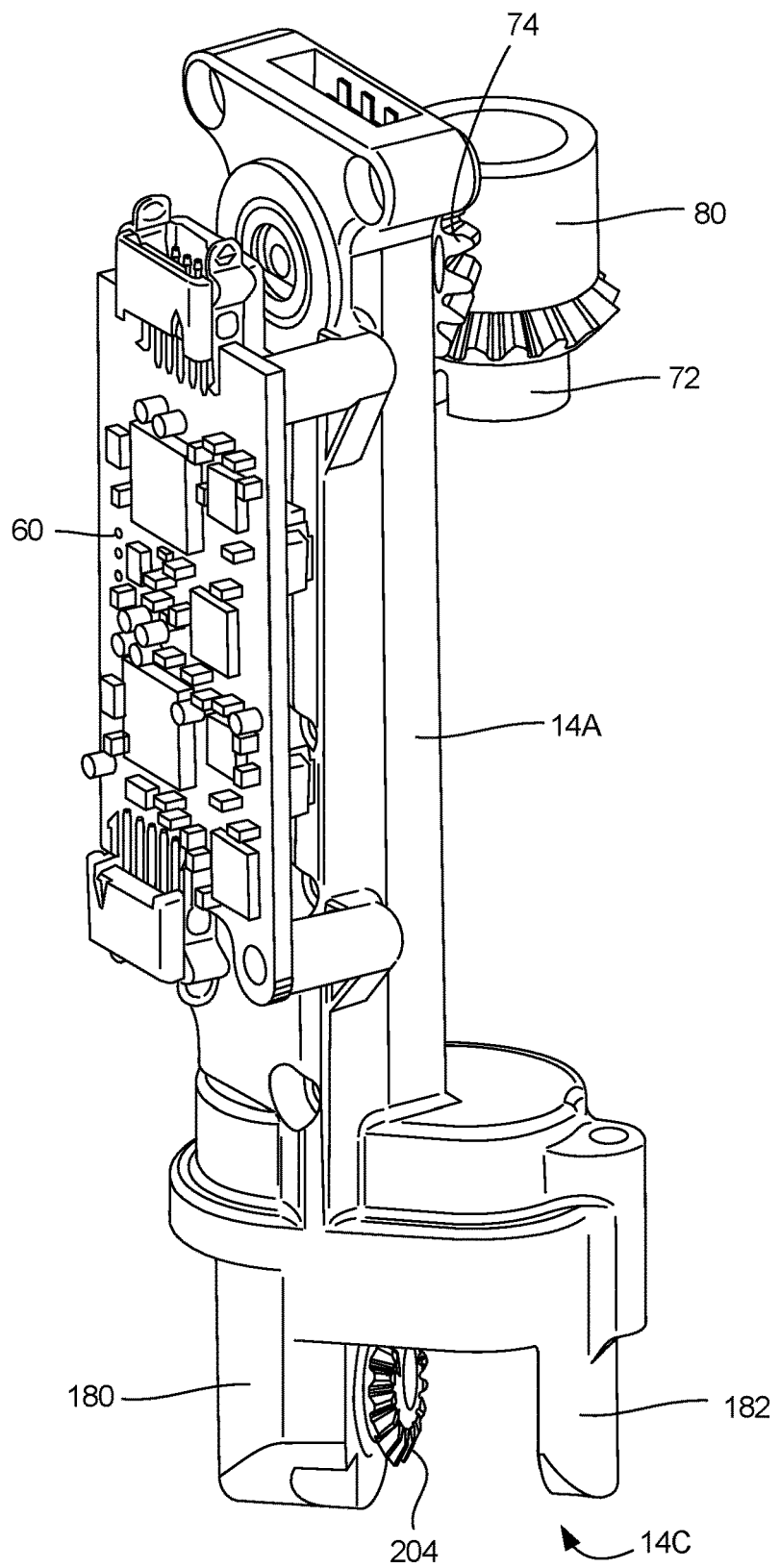
FIG. 8A is a perspective view of an upper arm of a robotic device, according to one embodiment.

As mentioned above, the right output bevel gear 74 is coupled via gear teeth to both the right upper bevel gear 70 and the right lower bevel gear 72. The output shaft 80 is supported by bearing 120, which is inset into the output bevel gear 74 as shown. In addition, the output shaft 80 is also supported by bearing 122, which is positioned in and supported by a proximal portion of the upper arm attached thereto, such as upper arm 14A as best shown in FIGS. 1 and 8A or any other upper arm as disclosed or contemplated herein. Further, the output bevel gear 74 is rotationally coupled to the proximal end of the upper arm (such as upper arm 14A), as best shown in FIGS. 7A and 8A and discussed below.

As best shown in FIG. 4A, the body 10 has two potentiometers: an upper arm potentiometer 124 and a driveshaft potentiometer 126. The upper arm potentiometer 124 is positioned around the output shaft 80 and coupled to the upper arm (such as upper arm 14A, as best shown in FIG. 7A) such that the potentiometer 124 can measure the relative angular displacement between the output shaft 80 and the upper arm (such as upper arm 14A). Further, the driveshaft potentiometer 126 is operably coupled to a potentiometer adapter 128, which is rotationally fixed to the driveshaft 30 such that rotation of the driveshaft 30 causes rotation of the adapter 128. The driveshaft potentiometer 126 measures the relative angular displacement between the driveshaft 30 and the body 10.

In addition, in one embodiment, the adapter 128 also functions in combination with the threaded bolt 130 to preload the bearing 90, thereby helping to provide support to the driveshaft 30. More specifically, the tightening of the bolt 130 in relation to the driveshaft 30 causes the potentiometer adapter 128 to make contact with the inner race of bearing 90. This causes the shoulder 132 of the driveshaft 30 to contact the inner race of bearing 94 and create a clamping force as the shoulder 132 is urged against the inner race of the bearing 94. (It should be noted here that the gap between the shoulder 132 and the bearing 94 is exaggerated in FIGS. 4A and 4B for easier depiction of the shoulder 132.) This clamping force helps to preload all of the bearings 90, 94, 96, 98, 100 that help to support the driveshaft 30. In certain alternative implementations, one or more spring washers or other known gap-filling components can be positioned between the shoulder 132 and the bearing 94 to reduce the amount of precision needed for machining etc.

Figure 4D:
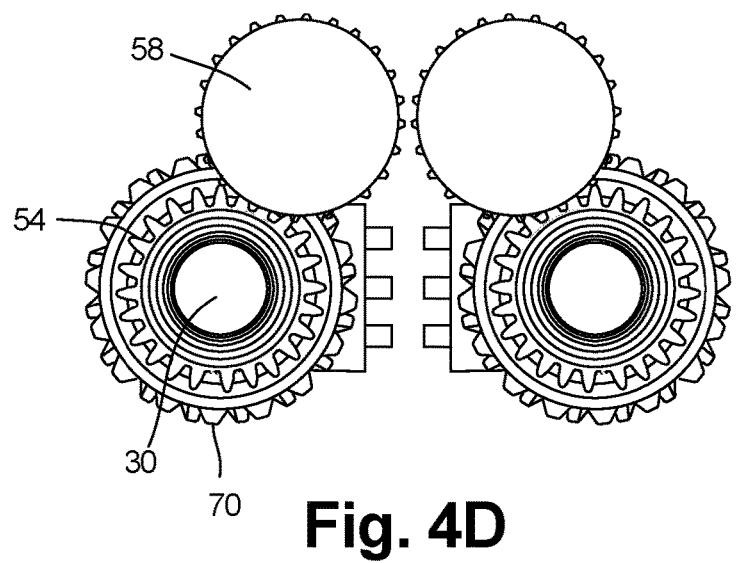
FIG. 4D is a cross-sectional top view of certain internal components of the device body of the robotic device of FIG. 1, according to one embodiment.

The shoulder drivetrain components described above and depicted in FIGS. 4A and 4B are concentric (or "nested") drivetrain components, thereby reducing the size requirements for the device body 12. That is, each shoulder of the device 10 uses a bevel gear set (such as the set of three bevel gears 70, 72, 74 described above with respect to the right shoulder 14D) that is driven by concentric driveshafts, thereby resulting in a reduced size or compacted design of the shoulder 14D and device body 12. As an example as best shown in FIGS. 4B and 4C, the distal portion of driveshaft 30 is disposed in or through the driven gear 76, the upper bevel gear 70, the output shaft 80, and the lower bevel gear 72, such that the driveshaft 30 is concentric with each of those components and is rotatable independently of driven gear 76 and upper bevel gear 70. Nesting this driveshaft 30 (and driveshaft 32 as well) makes it possible for both motors 58, 84 (as shown in FIG. 4C) to be positioned in the body 12 above the bevel set 70, 72, 74, thereby resulting in smaller overall cross-sectional dimensions of the body 12 since neither a motor nor a driveshaft needs to pass alongside the bevel gear set. This compact design is best depicted in FIG. 4D, which shows a cross-sectional cutaway view of an upper portion of the device body 10. As shown, the positioning of the driveshaft 30 concentrically with the gears 54 and 70, along with other components, requires less space within the device body 12 in comparison to any configuration in which the driveshaft 30 is not nested and instead is positioned alongside the gears 54, 70 and the motor 58. It is understood that this compact nested configuration could also be incorporated into higher degree of freedom robot designs as well.

Figure 5:
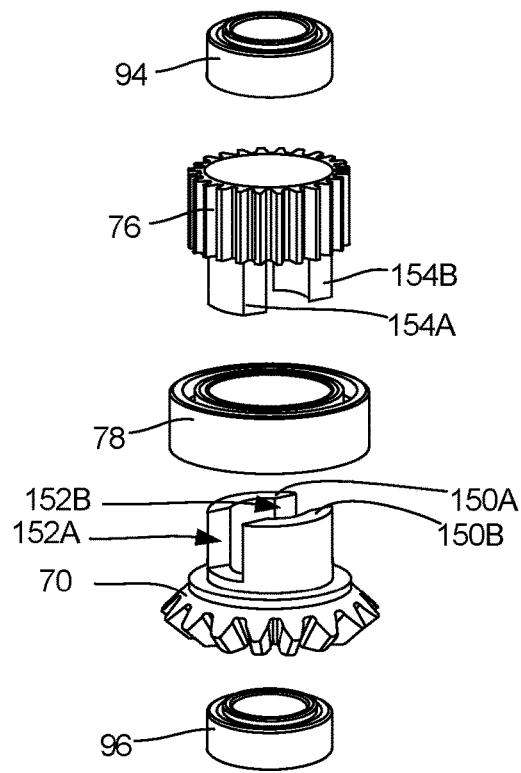
FIG. 5 is a perspective view of a bevel gear and a driven gear and related components, according to one embodiment.

FIG. 5 depicts one embodiment of the right upper bevel gear 70 and its coupling to the driven gear 76 in further detail. That is, the upper bevel gear 70 has two projections 150A, 150B that define two slots 152A, 152B. Further, the driven gear 76 has two projections 154A, 154B that are configured to be positionable within the slots 152A, 152B of the upper bevel gear 70 such that the driven gear 76 and upper bevel gear 70 are rotationally coupled to each other. That is, the two projections 154A, 154B mate with the slots 152A, 152B, thereby coupling the driven gear 76 and upper bevel gear 70 together. Further, the bearing 78 is positioned around the projections 150A, 150B and the projections 154A, 154B when they are coupled together, thereby helping to retain—radially—the mating of the projections 150A, 150B, 154A, 154B together. Alternatively, any known coupling mechanism or component for rotationally coupling two gears can be used to couple the driven gear 76 and the upper bevel gear 70. As further discussed above and depicted in FIGS. 4A and 4B, bearing 94 is inset into driven gear 76, and bearing 96 is inset into upper bevel gear 70. In addition, as best shown in FIGS. 4A and 4B in combination with FIG. 5, the preloading of the driveshaft 30 as discussed above helps to retain the coupling of the driven gear 76 and bevel gear 70. That is, the driveshaft 30 is positioned through the middle of the bearing 94, driven gear 76, bearing 78, bevel gear 70, and bearing 96 and constrains these components via the shoulder 132 being urged against the bearing 94 as discussed above.

Figure 6:
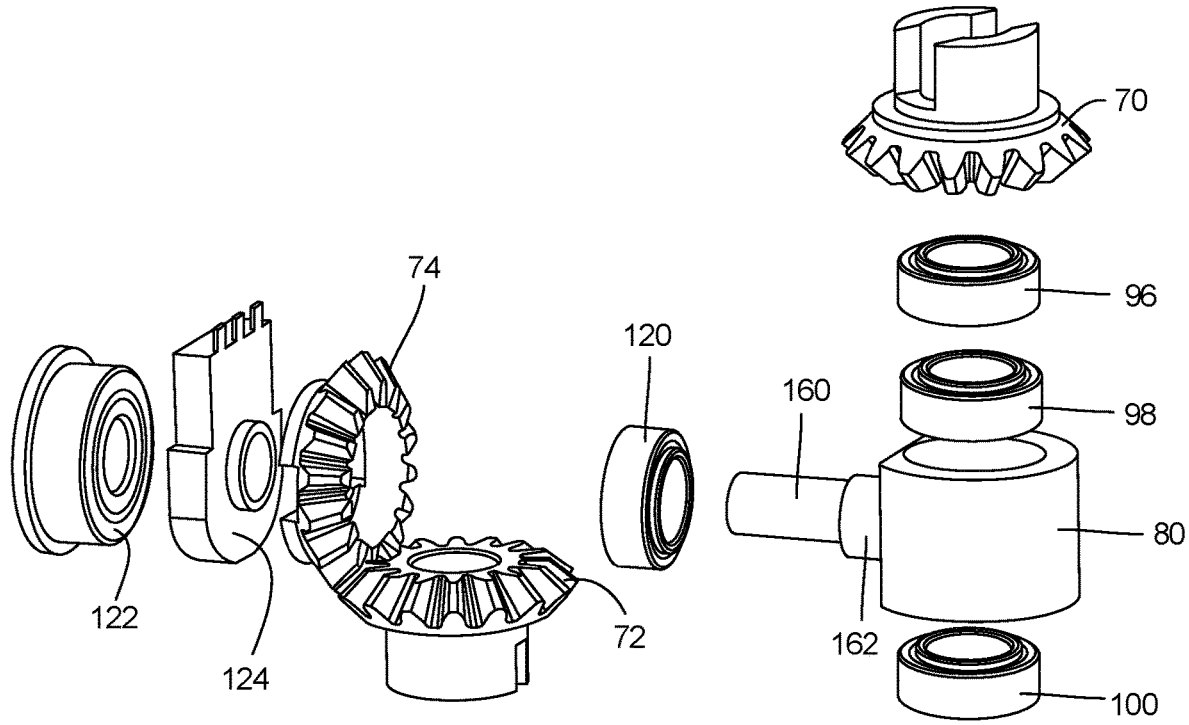
FIG. 6 is a perspective view of an output shaft, bevel gears, and related components, according to one embodiment.

FIG. 6 depicts an implementation of the output shaft 80 and its coupling to the bevel gears 70, 72, 74 in further detail. The output shaft 80 has an arm 160 that extends away from the driveshaft 30. As discussed above, bearing 98 is inset into the upper opening of output shaft 80, and bearing 100 is inset into the lower opening of the output shaft 80. It is understood that each of the bearings 98, 100 rest on internal shoulders (not shown) within the output shaft 80 and thus do not come into contact with each other. Further, the inner race of bearing 100 rests against the gear face of lower bevel gear 72. As mentioned above, the output shaft 80 is supported by bearings 120 and 122. Bearing 120 rests on the shoulder 162 of the arm 160 of output shaft 80 and further is inset in output bevel gear 74. The potentiometer 124 is positioned between output bevel gear 74 and bearing 122. Bearing 122, potentiometer 124, bevel gear 74, and bearing 120 are positioned over and axially constrained onto the arm 160 of output shaft 80 by a bolt (not shown) that is threadably coupled to the end of the arm 160. Further, it is understood that bearing 122, along with the potentiometer 124, and output bevel gear 74 are constrained to the upper arm (such as upper arm 14A as shown in FIGS. 7A and 8A).

Figure 7B:
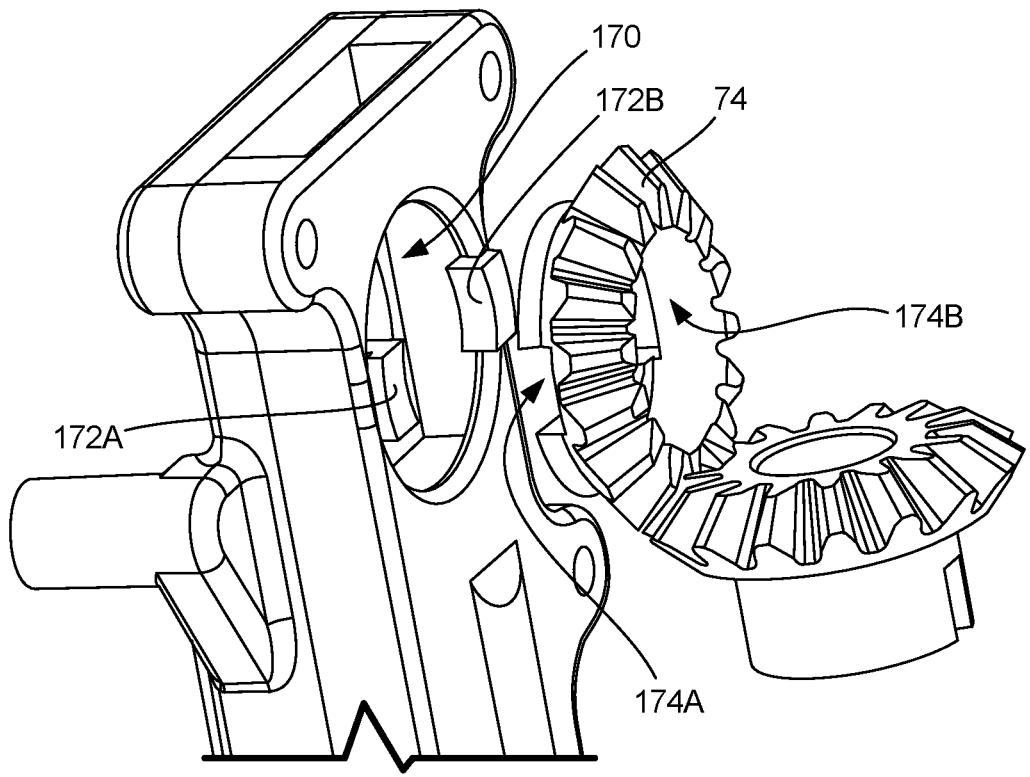
FIG. 7B is a perspective view of certain components of the right shoulder joint of FIG. 7A, according to one embodiment.

FIGS. 7A and 7B depict the right shoulder 14D, according to one embodiment. The upper arm 14A supports the potentiometer 124 such that the potentiometer 124 is disposed within the upper arm 14A in this implementation. Further, the upper arm 14A also supports bearing 122, which is disposed within an opening (not shown) in the arm 14A. As best shown in FIG. 7B, the upper arm 14A also has an opening 170 defined in the arm 14A, with two projections 172A, 172B positioned around the edge that defines the opening 170. The two projections 172A, 172B mate with slots 174A, 174B defined in the output bevel gear 74 such that the upper arm 14A is rotationally coupled to the output bevel gear 74. As such, rotation of the output bevel gear 74 causes rotation of the upper arm 14A around an axis defined by the bevel gear 74. Alternatively, any known coupling mechanism or component for rotationally coupling two components can be used to couple the upper arm 14A and the output bevel gear 74.

Figure 8B:
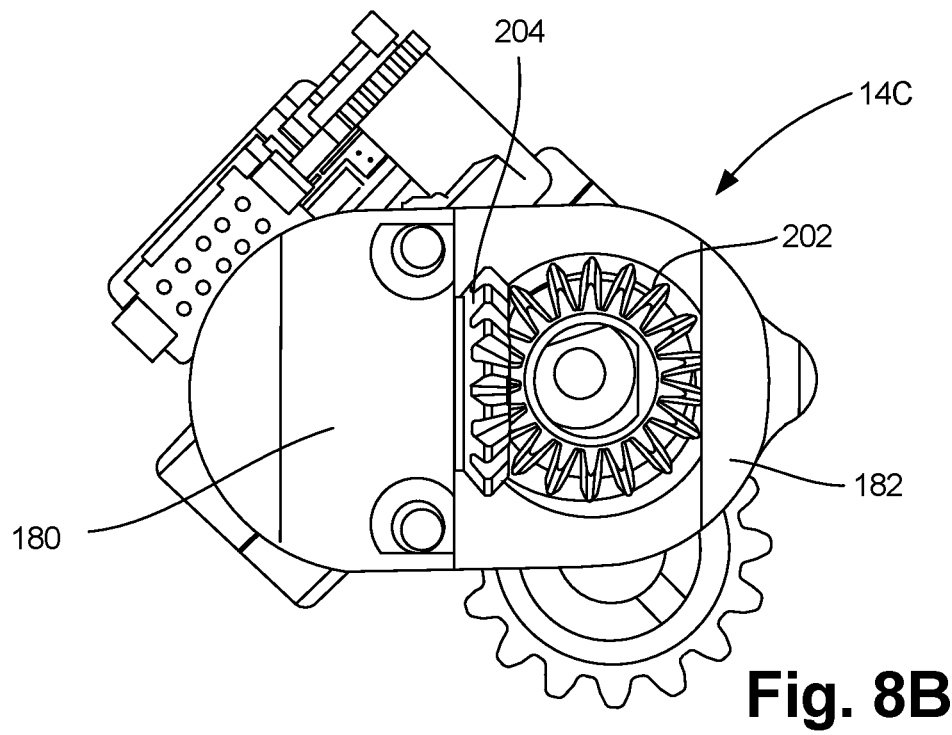
FIG. 8B is a bottom view of the upper arm of FIG. 8A, according to one embodiment.
Figure 8C:
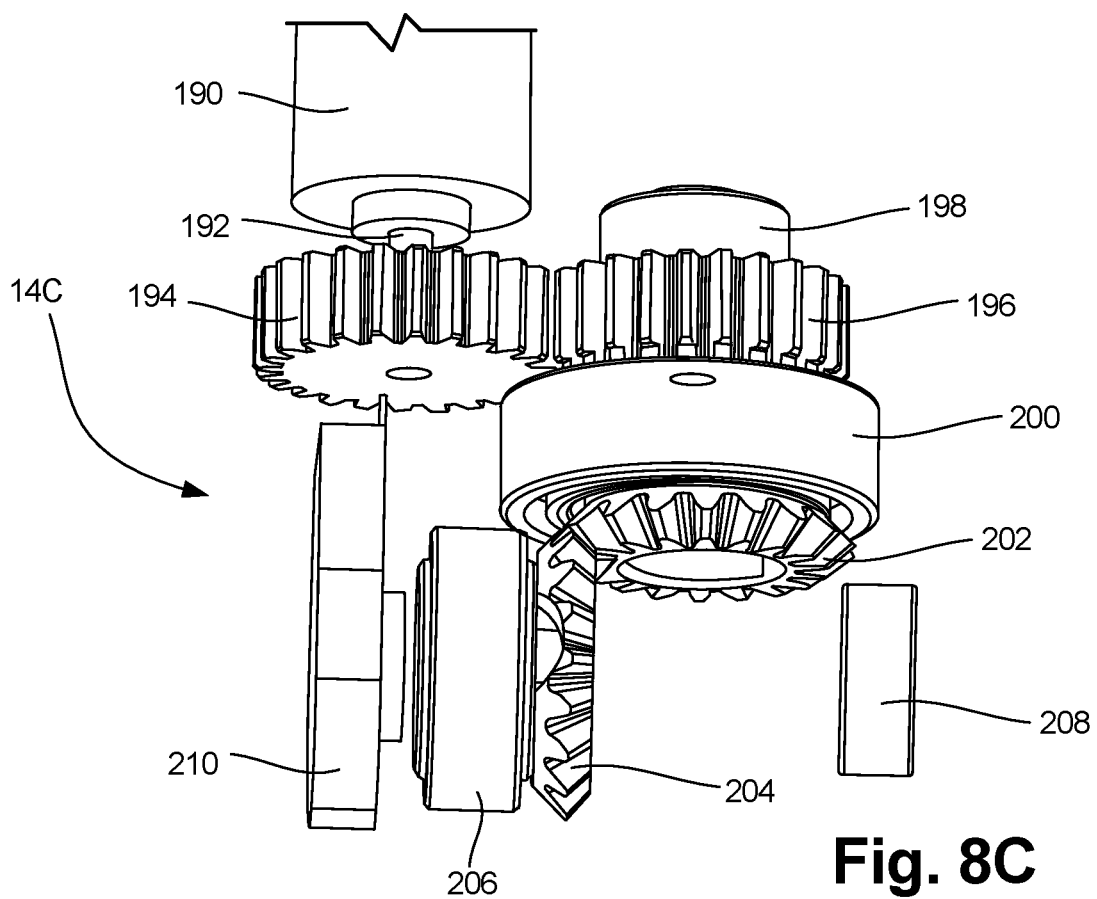
FIG. 8C is a perspective view of certain components of an elbow joint, according to one embodiment.

FIGS. 8A, 8B, and 8C, in accordance with one implementation, depict the upper arm 14A and the elbow joint 14C (also referred to herein as a "distal joint"). The elbow joint 14C is a right angle bevel gear set which is offset about 45 degrees in relation to the longitudinal axis of the upper arm 14A, thereby improving workspace characteristics. That is, the configuration of the elbow joint 14C as described herein results in the forearm (such as forearm 14B of FIG. 1, forearm 220 of FIGS. 9 and 10, or any other forearm disclosed or contemplated herein) being positioned at a better angle in relation to the target tissue from which to perform various procedures (in comparison to standard handheld laparoscopic tools that are positioned through laparoscopes, resulting in a larger, less desirable angle). In various embodiments, the offset can range from about 0 to about 180 degrees depending on the desired orientation for the arm 14.

In one embodiment, the upper arm 14A has a processor 60, which in this example is a circuit board 60. In this embodiment, the processor 60 is positioned on or coupled to an external surface of the upper arm 14A. Similarly, the device 10 depicted in FIG. 1 has several processors (like processor 60) positioned on exterior portions of the device 10. Alternatively, the processor 60 can disposed within an internal compartment or enclosure within the upper arm 14A, and, similarly, any other processors (like processor 60) such as those depicted in FIG. 1 can be disposed within internal compartments or enclosures within the device 10. The processor 60 can be coupled to one or more motors and control the actuation of those motors. Certain processors 60 can also be used for other functionalities other than motor control, and thus are not coupled to any motors. For example, one or more processors 60 could be coupled to one or more sensors that are configured to detect information regarding the state of the robotic device or some component thereof (such as a joint position or some electrical characteristic) or provide feedback regarding the environment and/or the patient (such as heart rate, cavity pressure, cavity humidity, etc.).

The elbow joint 14C is best shown in FIGS. 8A, 8B, and 8C. The upper arm 14A has a gear case 180 at or near the distal end of the arm 14A that contains or supports the second elbow bevel gear 204 and the potentiometer 210 (as best shown in FIG. 8C) as described in further detail below. Further, the upper arm 14A also has a bearing case 182 that extends distally from the upper arm 14A and contains or provides support for the bearing 208, which is also described in further detail below.

As best shown in FIG. 8C, the actuation (also referred to as "drivetrain") of the elbow joint 14C is created by a motor 190 disposed within the forearm 14A that has an output shaft 192 that is rotationally coupled to a drive gear 194. This drive gear 194 is rotationally coupled to driven gear 196, which is supported by bearing 198 and bearing 200. The bearing 200 is positioned adjacent to the first elbow bevel gear 202, which is rotationally coupled to the driven gear 196 such that rotation of the driven gear 196 causes rotation of the first elbow bevel gear 202. Further, in one implementation, the driven gear 196 can be axially coupled to the first elbow bevel gear 202 by a threaded bolt or other known coupling component that can be positioned through the driven gear 196. The first elbow bevel gear 202 is rotationally coupled to second elbow bevel gear 204, which is supported by bearing 206 and a forearm coupling link (such as the coupling link 228 depicted in FIG. 9), which is positioned through the opening defined in the center of the gear 204. Bearing 208 receives and supports the other end of the forearm rear link (such as link 228). In addition, as mentioned above, a potentiometer 210 is positioned adjacent to the bearing 206 and rotationally constrained by the gear case 180 (depicted in FIGS. 8A and 8B). The potentiometer 210 measures the rotational displacement between the gear case 180 and the forearm rear link (such as link 228 of FIG. 9), thereby measuring the amount of rotation of the forearm (such as forearm 14B of FIG. 1, forearm 220 of FIG. 9, or any other forearm disclosed herein) in relation to the upper arm 14A.

It is understood that certain alternative implementations have upper arms such as upper arm 14A that have no elbow joint and are not connected to a forearm. That is, certain device embodiments as contemplated herein can have two arms extending from the device body, but no forearms.

Figure 9:
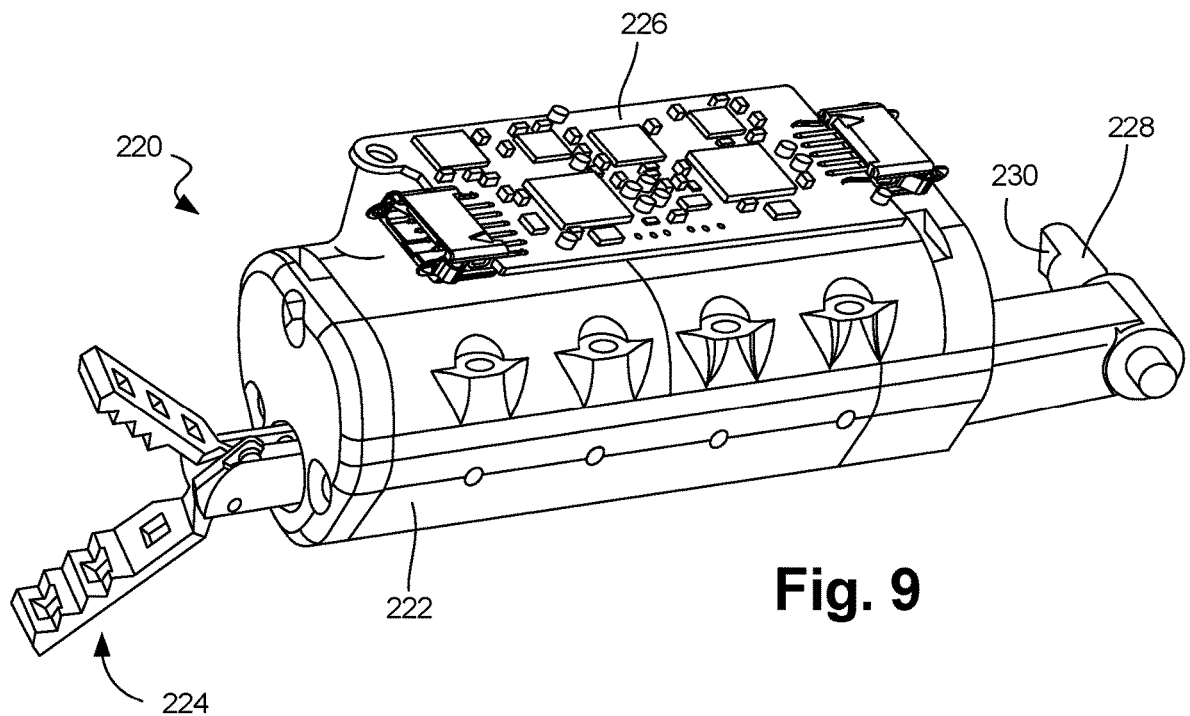
FIG. 9 is a perspective view of a forearm of a robotic device, according to one embodiment.

FIG. 9 shows one embodiment of a forearm 220 that can be incorporated into any of the robotic devices disclosed or contemplated herein. For example, in one implementation, the forearm 220 can be either the right 14B or left 16B forearm as shown in FIG. 1. Returning to FIG. 9, the forearm 220 has a forearm body 222, an end effector 224, a processor 226, and a coupling link 228. The body 222 supports the internal actuation components (such as motors) (not shown). As discussed elsewhere herein, the processor 226 is depicted as being attached to an external portion of the body 222, but it is understood that the processor 226 could be positioned within the body 222. As discussed above and further below, the coupling link 228 functions to couple the forearm 220 to an upper arm (such as upper arm 14A as described above). In this implementation, the link 228 can have a mating feature 230. More specifically, in this exemplary embodiment, the mating feature 230 is a flat surface defined on the link 228. Alternatively, any known mating feature can be used.

Figure 10:
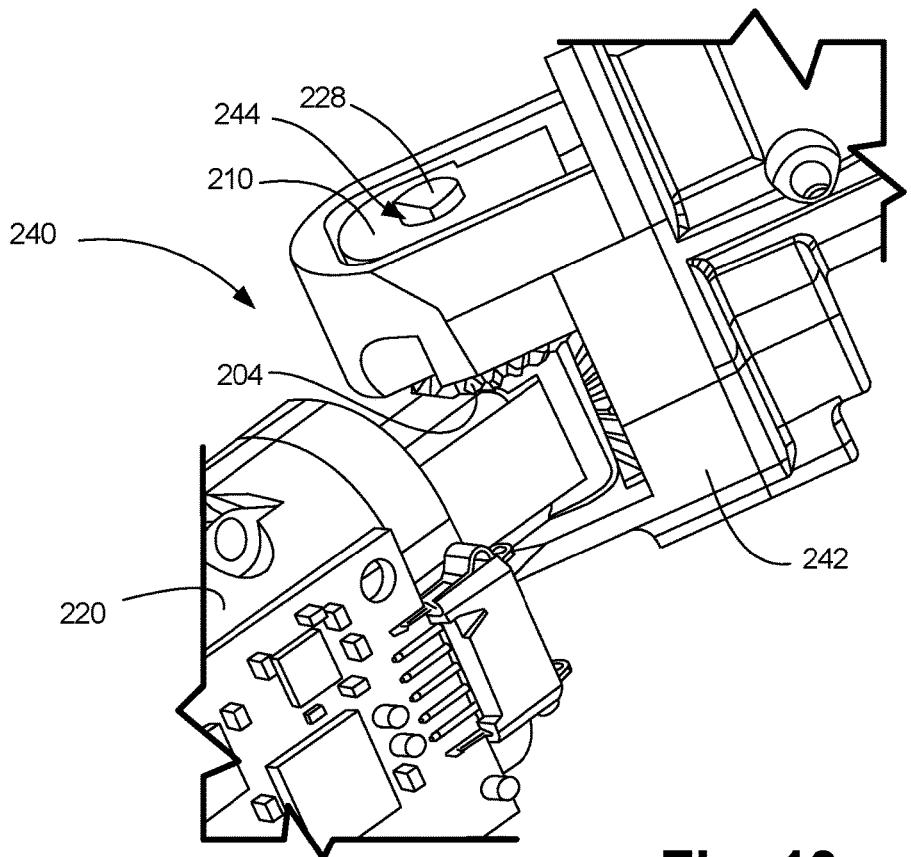
FIG. 10 is a perspective view of an elbow joint, according to one embodiment.

FIG. 10 depicts the elbow joint 240 between the forearm 220 and the upper arm 242 (which also could be the upper arm 14A described above or any other upper arm embodiment disclosed or contemplated herein). The forearm 220 is coupled to the upper arm 242 and to the second elbow bevel gear 204 in the upper arm 242 at the elbow joint 14C via the forearm coupling link 228. More specifically, the coupling link 228 is positioned through an opening (not shown) in the second elbow bevel gear 204 and through an opening 244 in the potentiometer 210 as well, thereby rotatably coupling the coupling link 228 to the upper arm 242. Further, the mating feature 230 (as shown in FIG. 9) mates with the opening 244 in the potentiometer 210 such that the rotation of the link 228 can be measured by the potentiometer 210.

Figure 13:
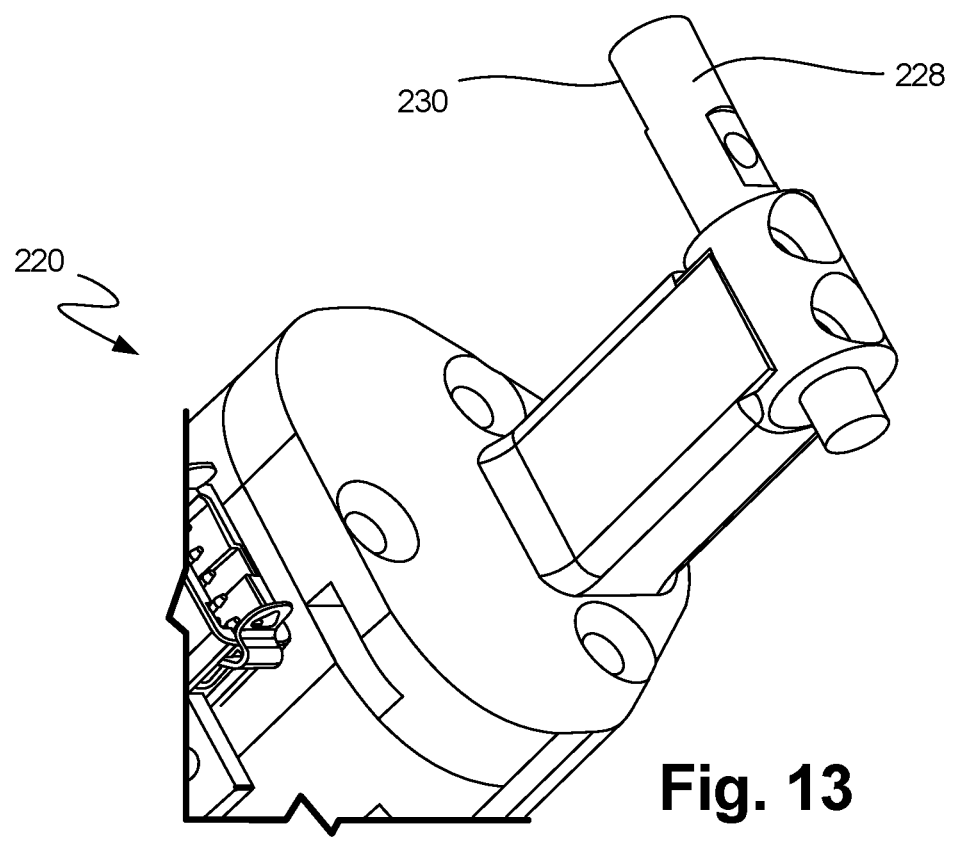
FIG. 13 is a perspective view of a proximal portion of a forearm, according to one embodiment.

FIG. 13 depicts the proximal portion of forearm 220, and more specifically a close-up view of the forearm coupling link 228 depicted in FIGS. 9 and 10 and discussed above. As explained in further detail above, the link 228 is used to couple the forearm 220 to an upper arm, and more specifically to couple the forearm 220 to the second elbow bevel gear 204 of the upper arm. As also discussed above, the mating feature 230 is configured to couple with the potentiometer 210.

Figure 11:
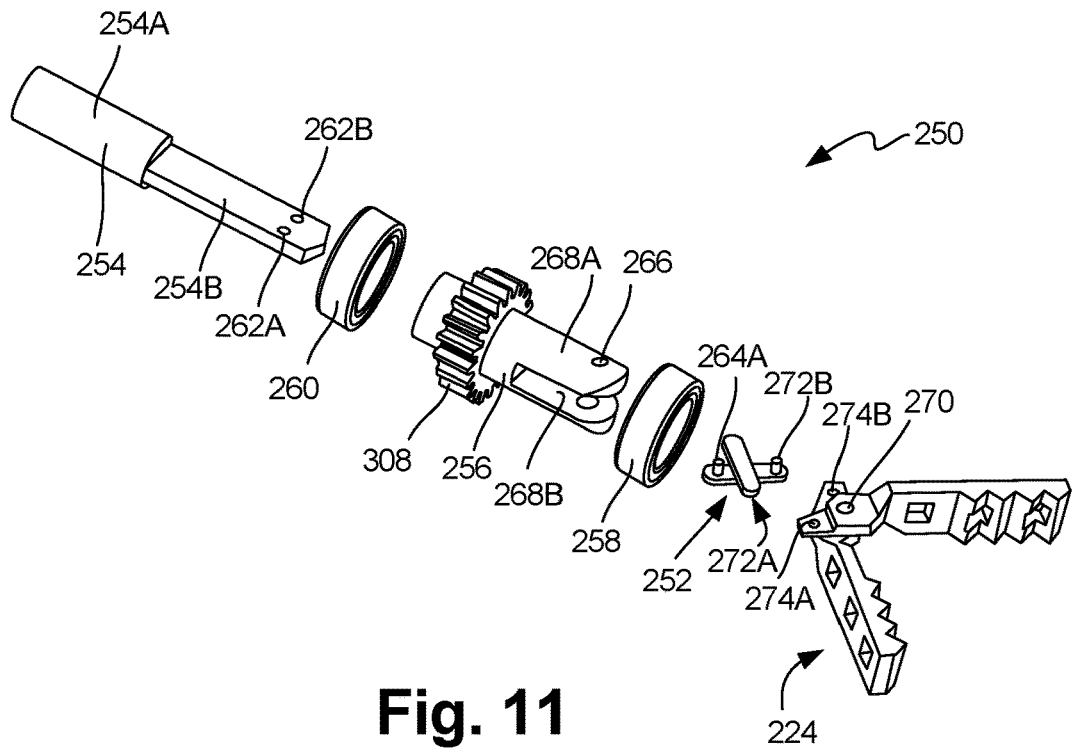
FIG. 11 is a perspective view of various components of an end effector drive mechanism, according to one embodiment.

FIG. 11 depicts the end effector drive mechanism 250 of the forearm 220. It is understood that the drive mechanism 250 is disposed within the body 222 of the forearm 220 (or any other forearm embodiment disclosed or contemplated herein). In this implementation, the end effector 224 is a set of graspers 224. The end effector drive mechanism 250 has grasper linkages 252, a drive pin 254, a drive yolk 256, and first and second bearings 258, 260. The graspers 224 are coupled to grasper linkages 252 via the grasper arm holes 274A, 274B such that actuation of the linkages 252 causes movement of the graspers 224. More specifically, the protrusions 272A, 272B on the distal ends of the linkages 252 are positioned within the holes 274A, 274B, thereby coupling the graspers 224 to the linkages 252. The drive pin 254 has a proximal length 254A with a circular cross-section and external threads (not shown) and a distal length 254B with a rectangular cross-section that is configured to be positioned within the bearing 260, the yolk 256, and the bearing 258. Further, the drive pin 254 has two holes 262A, 262B defined near the distal end of the drive pin 254. The holes 262A, 262B are configured to receive the projections 264A, 264B (not visible) on the grasper linkages 252.

In this specific implementation, during assembly, the drive pin 254 can be inserted from a originating proximal direction distally through the bearing 260, yolk 256, and bearing 258 to be positioned therein, thereby allowing for assembly of the drive mechanism 250 from a proximal or back portion of the forearm 220 (unlike known configurations that require assembly from the front). Assembly from the back allows the diameter of the proximal length 254A to be larger in size and further allows the threads (not shown) on the proximal length 254A to be coarser in pitch than the known, front-assembly configurations, thereby resulting in improved rigidity and durability of the drive mechanism 250. Alternatively, the components can be assembled by any known method use any known order of steps.

The drive yolk 256 has a gear 308 coupled to or integral with the yolk 256 and is supported by bearing 260 and bearing 258. Further, the yolk 256 has a pin hole 266 defined through the two prongs 268A, 268B of the yolk 256. The pin hole 266 is configured to receive a pin (not shown) that is also positioned through the pin hole 270 on the set of graspers 224, thereby coupling the yolk 256 to the graspers 224.

Figure 12:
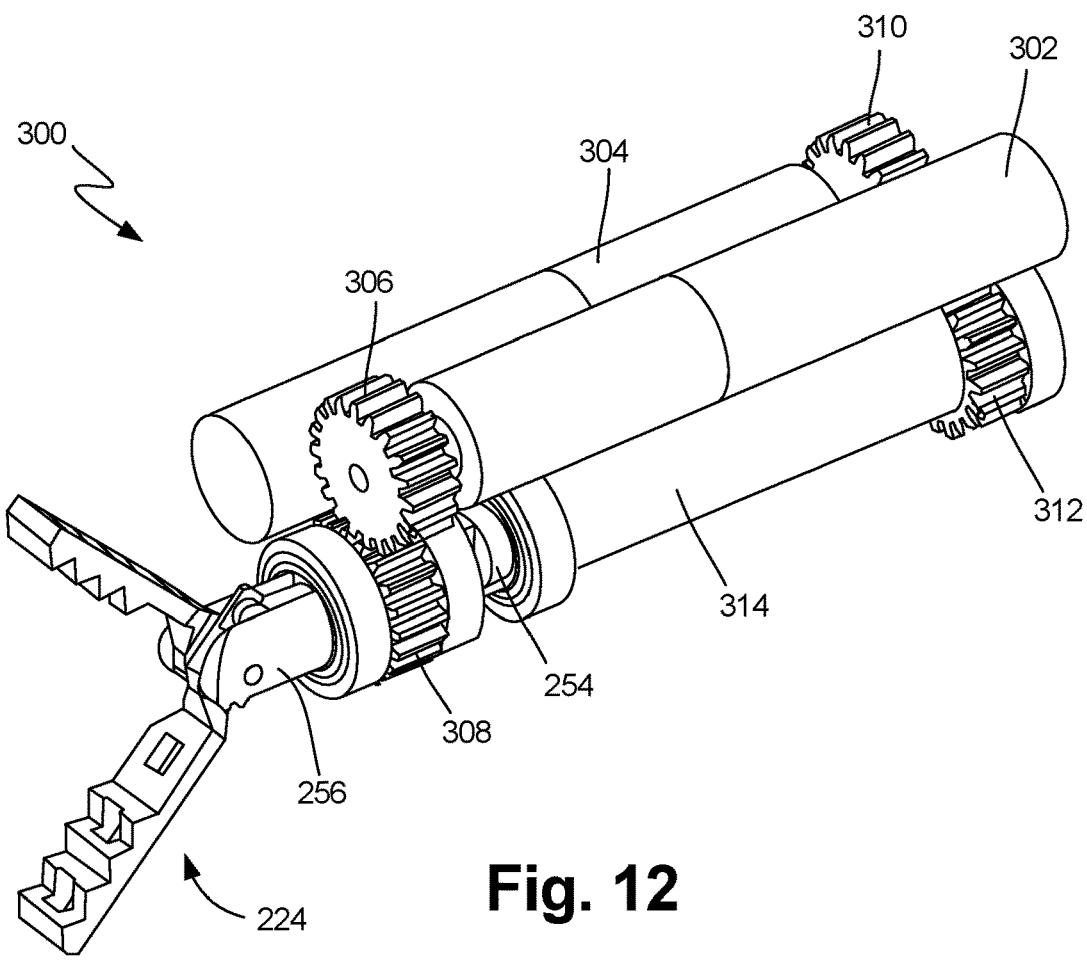
FIG. 12 is a perspective view of end effector actuation mechanisms, according to one embodiment.

The end effector actuation mechanisms 300 are depicted in FIG. 12, in accordance to one embodiment. The mechanisms 300 are made up of two actuation components 302, 304, which, in this example, are motors 302, 304. Motor 302 actuates the grasper assembly 224 to rotate around the longitudinal axis of the drive yolk 256. More specifically, motor 302 is rotationally coupled to a drive gear 306, which is rotationally coupled to the driven gear 308. As discussed above, the driven gear 308 is rotationally coupled to the drive yolk 256. Hence, actuation of the motor 302 causes rotation of the drive gear 306, which causes rotation of driven gear 308, which causes rotation of the drive yolk 256, which causes rotation of the entire grasper assembly 224.

The other motor 304 of the actuation mechanisms 300 actuates the set of graspers 224 to open and close by actuating the end effector drive mechanism 250 described above (and depicted in FIG. 11). That is, motor 304 is rotationally coupled to drive gear 310, which is rotationally coupled to driven gear 312. The driven gear 312 is rotationally coupled to a lead nut 314, which is coupled to the drive pin 254 of the drive mechanism 250 as discussed above. More specifically, the threaded proximal length 254A of drive pin 254 is disposed within a lumen (not shown) defined within the lead nut 314. The lumen (not shown) is threaded such that the threaded proximal length 254A is threadably coupled to the threaded lumen (not shown) of the lead nut 314. As such, rotation of the lead nut 314 causes the drive pin 254 to translate axially as a result of the threaded coupling between the nut 314 and pin 254. Thus, actuation of the motor 304 causes rotation of drive gear 310, which causes rotation of driven gear 312, which causes rotation of the lead nut 314, which causes axial translation of the drive pin 254, which causes the graspers 224 to open and close as discussed above.

Figure 14:
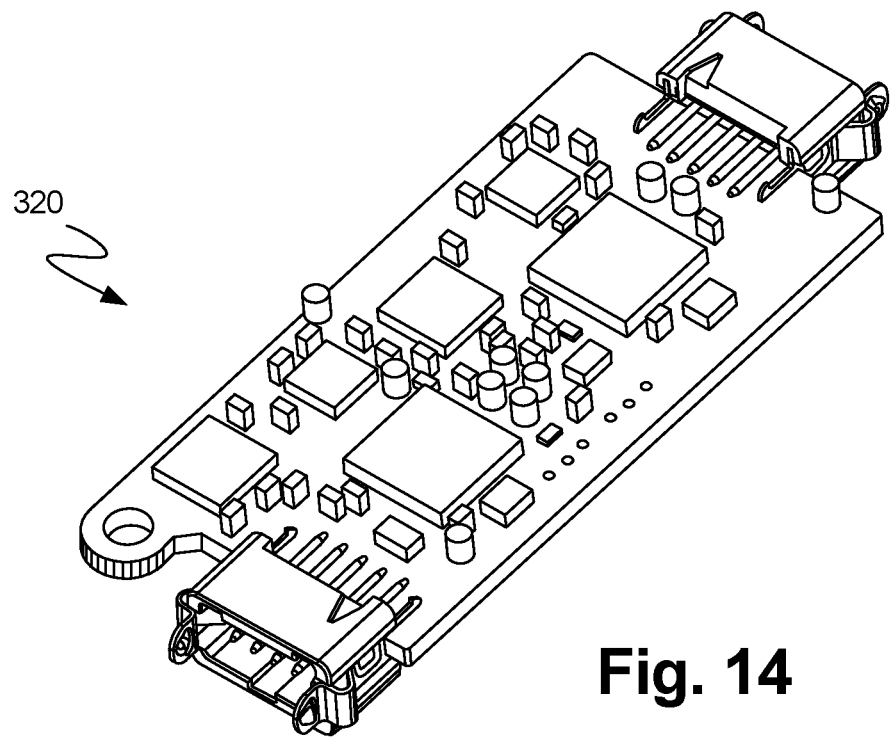
FIG. 14 is a perspective view of a processor, according to one embodiment.

One exemplary implementation of a processor 320 is depicted in FIG. 14. As discussed above, it is understood that processors such as processor 230 are used throughout the robotic device embodiments disclosed or contemplated herein. In certain implementations, one or more of the processors such as processor 230 can be a circuit board 230. Each of the processors 230 can be coupled to the motors and/or joints of the device, thereby transmitting and receiving communication signals thereto. In further embodiments, the processors 230 can also transmit power to and/or receive power from the motors and/or joints. In certain specific embodiments, communication with the processor 230 is done through the RS485 protocol. In further implementations, each of the processors 230 are circuit boards having two nearly identical processors and drive circuitry that provide redundancy and allow for separate analysis and debugging of the systems.

It is understood that the motors described herein are brushed motors. In one implementation, the motors are 8 mm and/or 10 mm Faulhaber™ motors. Alternatively, the motors can be brushless motors. In a further embodiment, the motors can be any known motors for use in robotic surgical devices. It is further understood that any types of actuation mechanisms can be substituted for any of the motors described herein.

It is understood that the various bearing configurations and positions within these embodiments can be changed such that there are more or fewer bearings in the same or different positions as desired.

Another forearm 400 embodiment that can be used with the various robotic device embodiments described above is depicted in FIG. 15. The forearm 400 has a cautery end effector 402 that also provides suction and irrigation. In addition, the end effector 402 is rotatable around its longitudinal axis. As is understood in the art, suction is used to remove fluid and small pieces of tissue from the patient during a procedure. Further, irrigation relates to the flooding of a fluid, generally saline, in order to clean a surface and to clear away blood in order to identify and locate bleeding.

Figure 15:
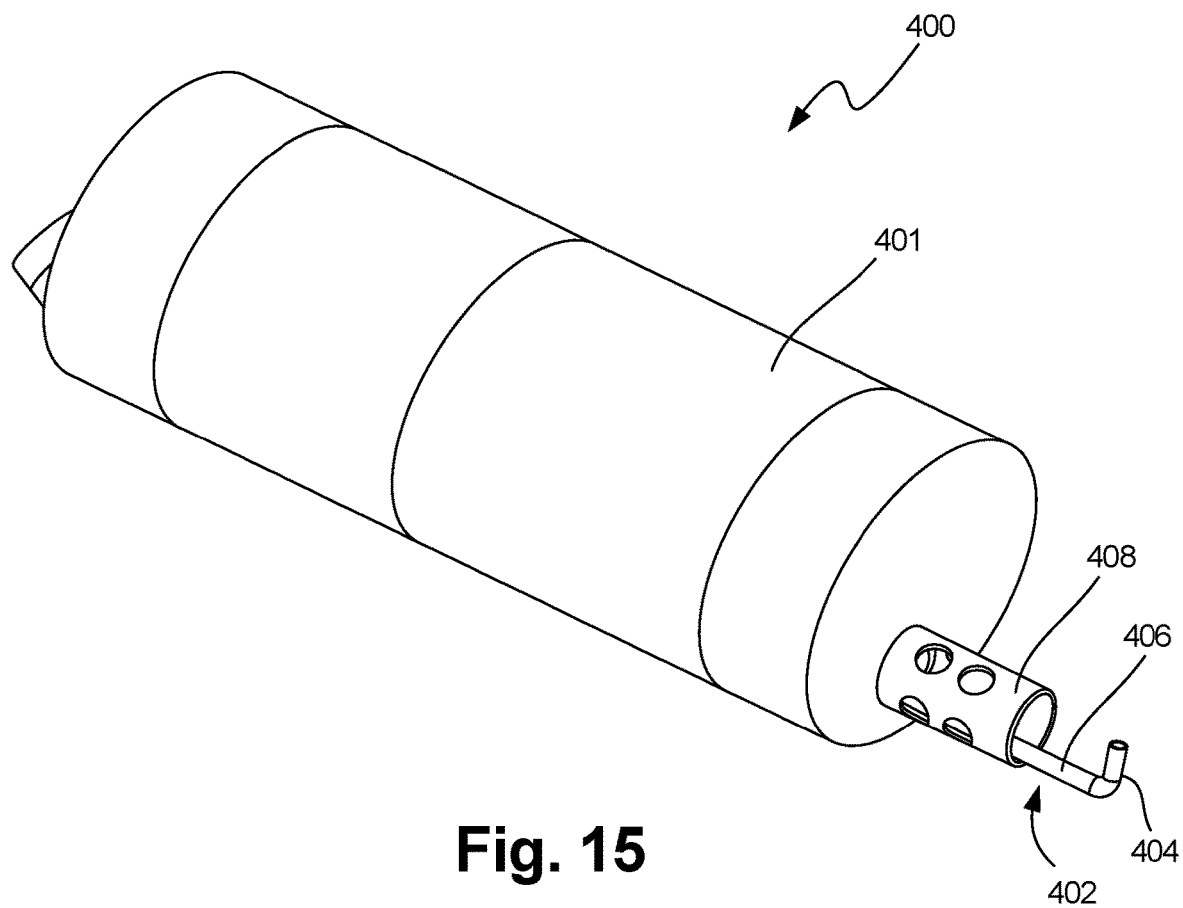
FIG. 15 is a perspective view of a cautery end effector with suction and irrigation capabilities, according to one embodiment.
Figure 16A:
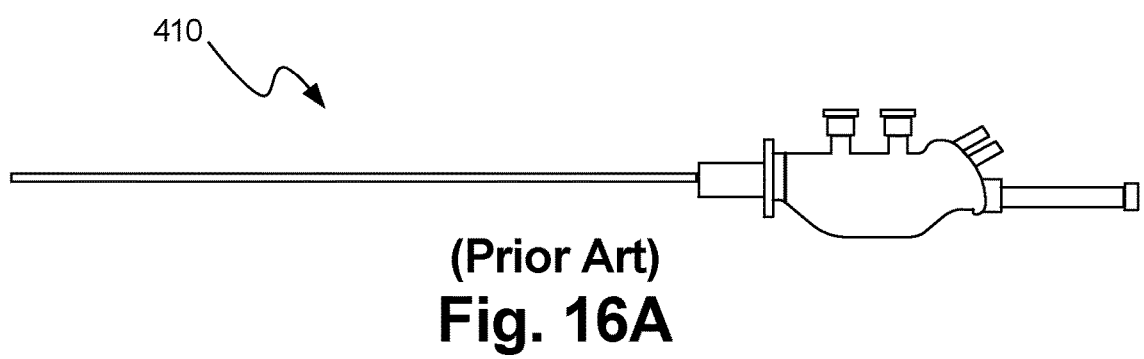
FIG. 16A is a side view of a known SurgiWand™ device.
Figure 16B:
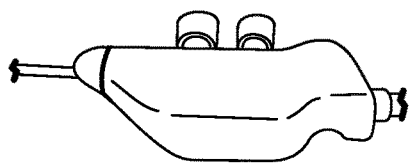
FIG. 16B is a perspective view of a portion of the known SurgiWand™ device.
Figure 16C:
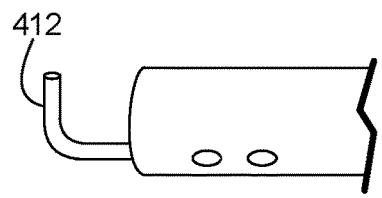
FIG. 16C is a side view of the cautery end effector of the known SurgiWand™ device.

The forearm 400 implementation improves upon the known SurgiWand™ device 410 depicted in FIGS. 16A-16C, which also combines a monopolar hook cautery 412 with suction and irrigation capabilities. The specific forearm 400 embodiment as shown in FIG. 15 provides a cautery end effector 402 having suction and irrigation on a forearm 400 of a robotic device that can be positioned entirely within a cavity of a patient or positioned in an incision (including a single incision) such that the device can perform a procedure within the patient's cavity.

Figure 17A:
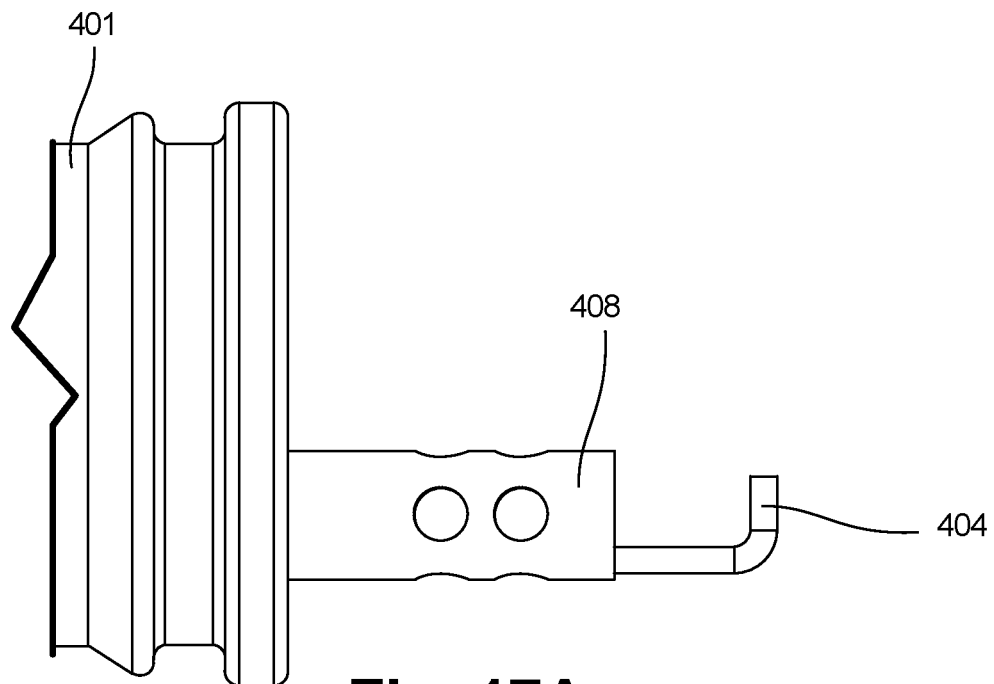
FIG. 17A is a side view of the cautery hook and extendable sleeve of the cautery end effector of FIG. 15 in which the extendable sleeve is in the retracted position, according to one embodiment.
Figure 17B:
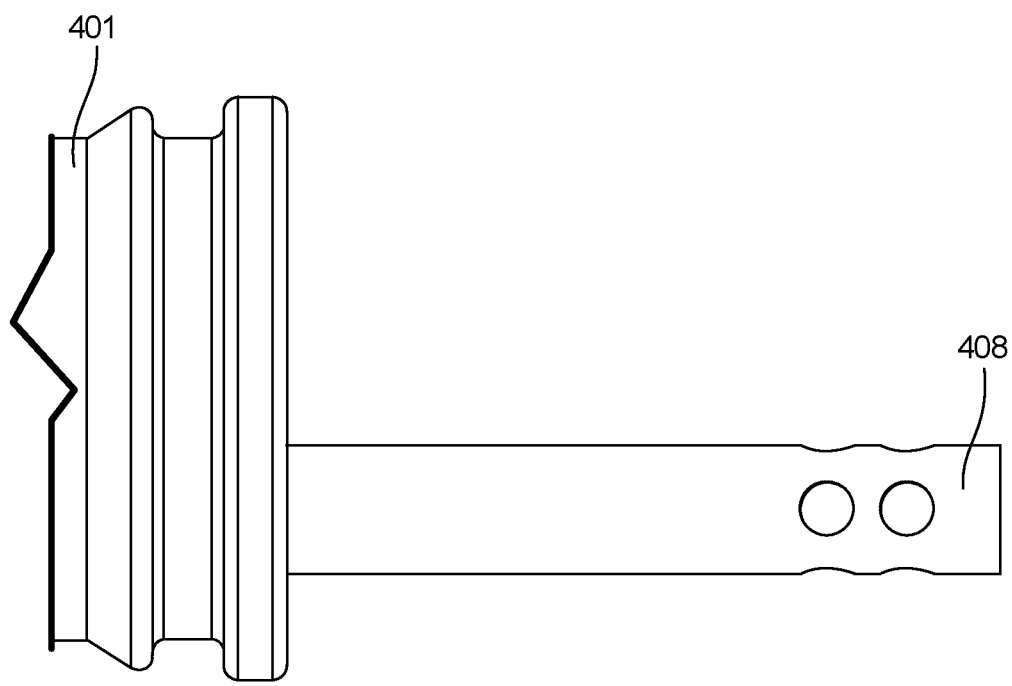
FIG. 17B is a side view of the cautery hook and extendable sleeve of the cautery end effector of FIG. 15 in which the extendable sleeve is in the extended position, according to one embodiment.

As best shown in FIG. 15, the forearm 400 has a forearm body 401, and the cautery end effector 402 has a cautery hook 404, a distal cautery shaft 406, and an extendable sleeve 408. As best shown in FIGS. 17A and 17B, the extendable sleeve 408 can move between a retracted position as shown in FIG. 17A and an extended position as shown in FIG. 17B. In the retracted position, the cautery hook 404 is exposed and can be used to perform a cauterization, while in the extended position, the sleeve 408 encloses and protects the hook 404 such that the hook 404 cannot make inadvertent contact with any tissues. Thus, during a procedure, the sleeve 408 can be positioned in its extended position when the cautery hook is not being used—especially during positioning of the robotic device and/or the forearm 400. Once the forearm 400 (and thus the end effector 402) is positioned as desired, the sleeve 408 can be retracted to its retracted position so that the cautery hook 404 is exposed and can be used to cauterize a target tissue.

Figure 18:
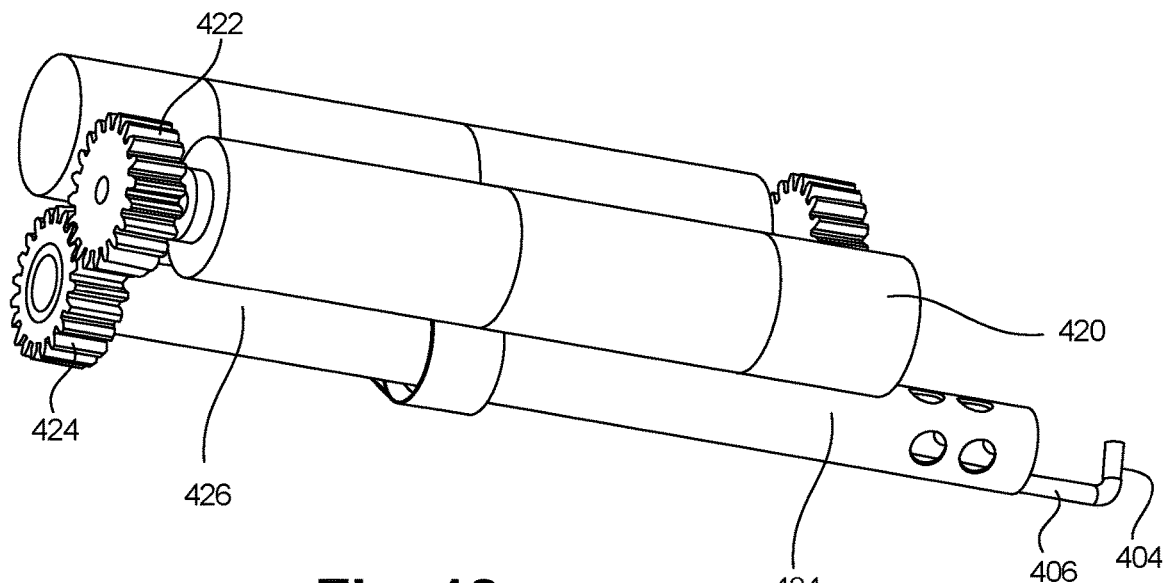
FIG. 18 is a perspective view of end effector actuation components, according to one embodiment.
Figure 19:
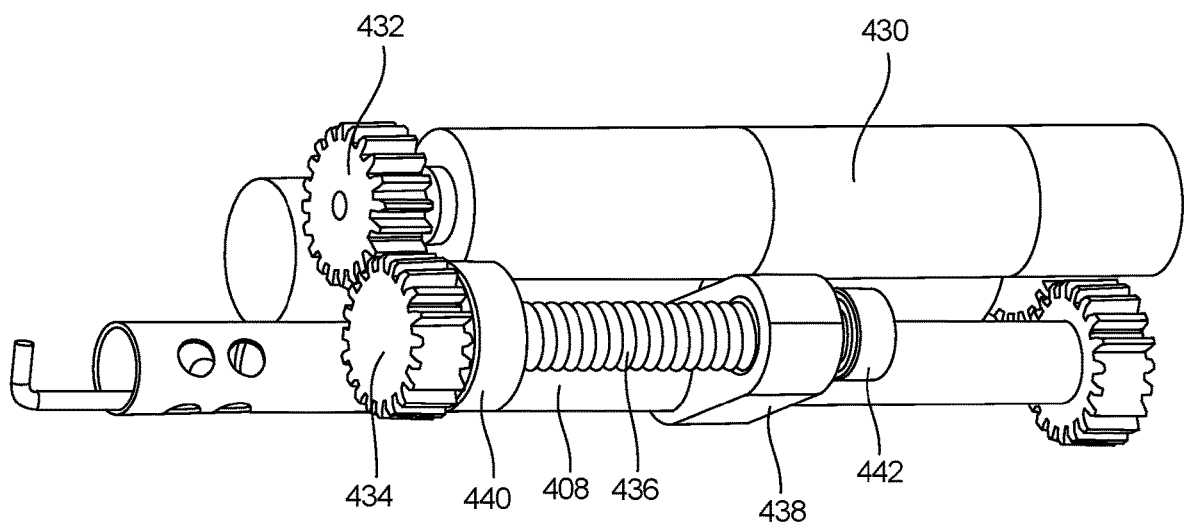
FIG. 19 is another perspective view of the end effector actuation components of FIG. 18, according to one embodiment.

The actuation components used to operate the end effector 402 are depicted in FIGS. 18 and 19, according to certain implementations. More specifically, FIG. 18 best depicts one embodiment of the components that operate to cause the end effector 402 to rotate around its longitudinal axis. As shown in FIG. 18, enclosed within the forearm body 401 (as shown in FIG. 15) is an actuation component 420 that in this example is a motor 420. The motor 420 is rotationally coupled to drive gear 422, which is rotationally coupled to driven gear 424. The driven gear 424 is rotationally coupled to the proximal cautery shaft 426 (which is coupled to the distal cautery shaft 406). In accordance with one embodiment, the proximal cautery shaft 426 can be supported by one or more bearings (not shown). The shaft 426 can also be electrically coupled to a flexible electrical contact (not shown) that is slideably disposed along the length of the shaft 426 such that it is positioned around and in contact with the circumference of the shaft 426. The electrical contact is electrically coupled to an external cautery generator that is located at a location that is external to the patient. In one alternative embodiment, the proximal and distal cautery shafts constitute a single, unitary cautery shaft.

FIG. 19 shows one implementation of the components that operate to cause the sleeve 408 to move between its retracted and extended positions. As shown in FIG. 19, the forearm body 401 also has an actuation component 430 that in this example is a motor 430. The motor 430 is rotationally coupled to drive gear 432, which is rotationally coupled to driven gear 434. The driven gear 434 is rotationally coupled to a threaded leadscrew 436, and both are supported by bearings 440, 442. The leadscrew 436 is coupled to a nut 438. More specifically, the nut 438 has an internal, threaded lumen through which the leadscrew 436 is positioned such that the external threads of the leadscrew 436 are threadably coupled to the internal threads of the nut 438. The nut 438 is constrained such that it cannot rotate. More specifically, in this particular embodiment, the nut 438 is shaped and positioned within the body 401 of the forearm 400 such that the nut 438 does not rotate when the leadscrew 436 is rotated. Further, the nut 438 is coupled to the retractable sleeve 408 such that movement of the nut 438 causes movement of the sleeve 408. When the motor 430 is actuated, the drive gear 432 rotates, thereby rotating the driven gear 434. Rotation of the driven gear 434 causes rotation of the leadscrew 436, which causes the nut 438 to translate axially, which causes the sleeve 408 to extend or retract. As best shown in FIGS. 18 and 19, the sleeve 408 slides along and thus is supported by the proximal cautery shaft 426.

Figure 20:
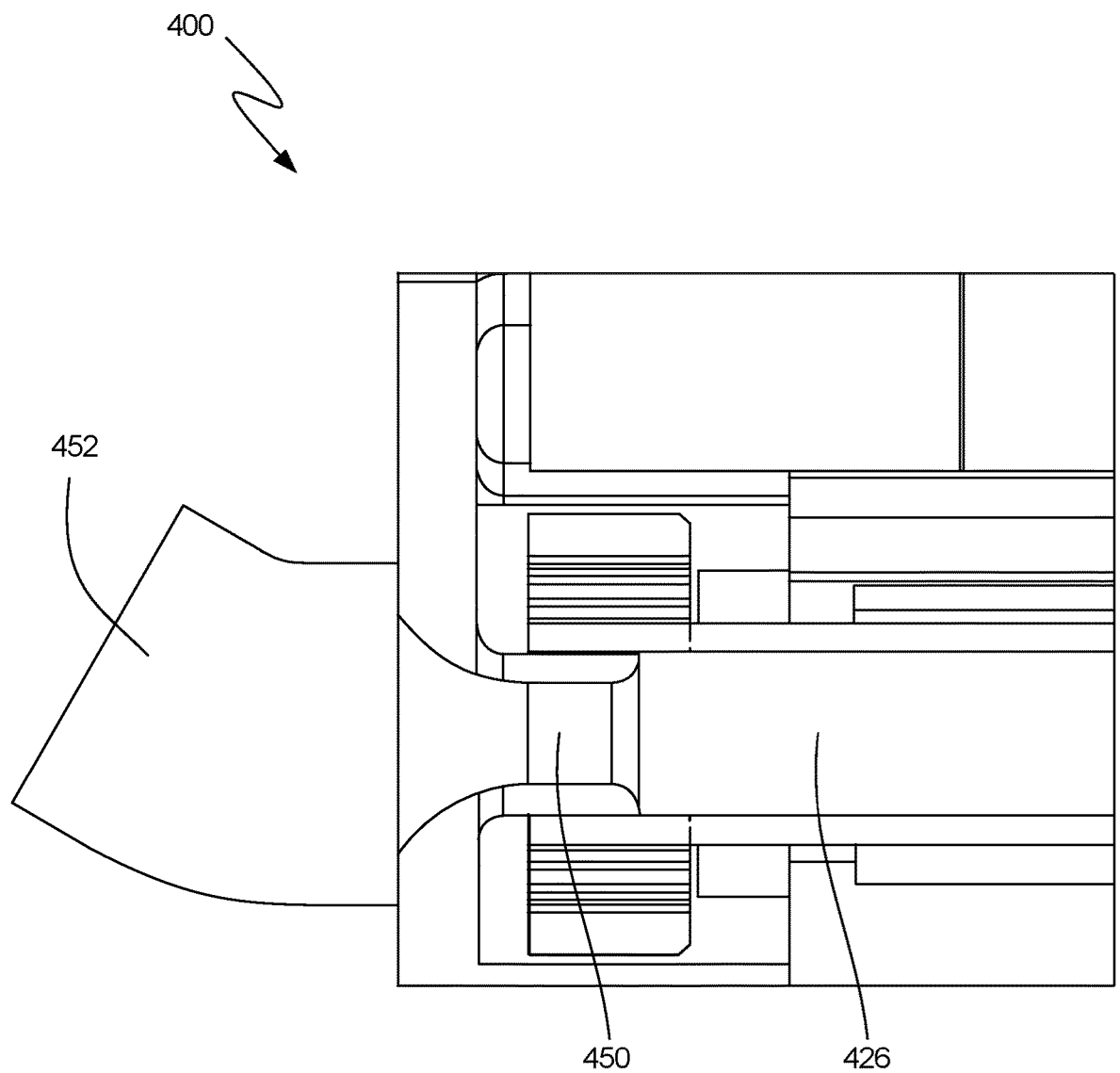
FIG. 20 is a side view of the proximal portion of a cautery end effector with suction and irrigation capabilities, according to one embodiment.

FIG. 20 depicts a proximal portion of the forearm 400, showing the proximal end of the proximal cautery shaft 426. The proximal end of the shaft 426 has a concentric port 450 that connects an external suction/irrigation line to the cautery shaft 426. More specifically, the port 450 connects to the cautery shaft 426 and further connects to external port 452. The concentric port 450 may or may not have a sealing feature between the port 450 itself and the cautery shaft 426. Both the suction and irrigation aspects share a single lumen that extends to the surgical site in the cautery shaft 426.

The relative location of the valve system in relation to the functional tip of the device plays a large role in the amount of dead space in the system. Dead space is the volume that is not directly controlled by the valve. In the case of the prior art SurgiWand™ device, the entire volume of the cautery shaft is dead space since—for example—irrigation does not stop when the valve is released but rather after the irrigation fluid has been drained from the shaft. Minimizing that dead space can result in better reaction times for the system. One method for limiting that dead space would be to run two lumens to the forearm and then have them combine with the single cautery shaft. In one embodiment of this design, the valves are located at the back of the forearm 400. In the preferred embodiment, the valves are located extracorporeal to the patient and the lines rely on the surface tension and produced vacuum of the irrigation fluid to prevent unintended drainage of the fluid.

It is understood that alternative embodiments of the forearm with the cautery end effector can use pneumatics, hydraulics, shape memory metals, or alternative drive methods to further improve the behavior of the suction/irrigation sleeve. In further implementations, brushless motors can be used. In addition, certain embodiments have a retractable sleeve that has additional holes along the outer edge and extending upwards along the axis of the sleeve. These holes can help to prevent damaging forces during occlusion of the suction tip. In yet another alternative implementation, the suction/irrigation configuration with the single lumen extending along the length of the forearm could also be used in other types of forearms and/or end effectors, such as graspers or scissors.

There are certain advantages to these embodiments of a cautery end effector. For example, the surgeon does not need change the control modality at all since the functional point of the cautery is also the functional point of suction/irrigation system. Further, there is also added benefit in how the cautery is allowed to roll, because the orientation of the hook can play a big role in its effectiveness.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

What is claimed is:

1. A robotic device comprising:
    (a) an elongate device body comprising:
        (i) a first motor disposed within the elongate device body;
        (ii) a first driveshaft operably coupled to the first motor and to a first lower gear; and
        (iii) a second motor disposed within the elongate device body and substantially coaxially with the first motor, the second motor operably coupled to a first upper gear;
    (b) a first shoulder joint comprising a first output shaft operably coupled to a first output gear, wherein the first output gear is operably coupled to the first upper and first lower gears; and
    (c) a first arm operably coupled to the first shoulder joint.

2. The robotic device of claim 1, wherein the first arm is a first upper arm, wherein the device further comprises a first forearm operably coupled to the first upper arm.

3. The robotic device of claim 2, further comprising a first end effector operably coupled to the first forearm.

4. The robotic device of claim 1, further comprising:
    (a) a third motor disposed within the elongate device body;
    (b) a second driveshaft operably coupled to the third motor and to a second lower gear;
    (c) a fourth motor disposed within the elongate device body and substantially coaxially with the third motor, the fourth motor operably coupled to the second upper gear;
    (d) a second shoulder joint comprising a second output shaft operably coupled to a second output gear, wherein the second output gear is operably coupled to the second upper and second lower gears; and
    (e) a second arm operably coupled to the second shoulder joint.

5. The robotic device of claim 4, wherein the second arm is a second upper arm, wherein the device further comprises a second forearm operably coupled to the second upper arm.

6. The robotic device of claim 5, further comprising a second end effector operably coupled to the second forearm.

7. The robotic device of claim 1, wherein the second motor is disposed distal of the first motor within the elongate device body.

8. The robotic device of claim 1, wherein the first and second motors are disposed proximal of the first shoulder joint within the elongate device body.

9. A robotic device comprising:
    (a) an elongate device body comprising:
        (i) a first shoulder gear set, comprising:
            (A) a first upper gear;
            (B) a first lower gear;
            (C) a first output gear operably coupled to the upper and lower gears;
        (ii) a first motor disposed within the elongate device body;
        (iii) a first driveshaft operably coupled to the first motor and to the first lower gear; and
        (iv) a second motor disposed within the elongate device body and substantially coaxially with the first motor, the second motor operably coupled to the first upper gear;
    (b) a first shoulder joint comprising a first output shaft operably coupled to the first output gear; and
    (c) a first arm operably coupled to the first shoulder joint.

10. The robotic device of claim 9, wherein the first arm is a first upper arm, wherein the device further comprises a first forearm operably coupled to the first upper arm.

11. The robotic device of claim 10, further comprising a first end effector operably coupled to the first forearm.

12. The robotic device of claim 9, further comprising:
    (a) a second shoulder gear set, comprising:
        (i) a second upper gear;
        (ii) a second lower gear;
        (iii) a second output gear operably coupled to the second upper and second lower gears;
    (b) a third motor disposed within the elongate device body;

(c) a second driveshaft operably coupled to the third motor and to the second lower gear;

(d) a fourth motor disposed within the elongate device body and substantially coaxially with the third motor, the fourth motor operably coupled to the second upper gear;

(e) a second shoulder joint comprising a second output shaft operably coupled to the second output gear; and (f) a second arm operably coupled to the second shoulder joint.

13. The robotic device of claim 12, wherein the second arm is a second upper arm, wherein the device further comprises a second forearm operably coupled to the second upper arm.

14. The robotic device of claim 13, further comprising a second end effector operably coupled to the second forearm.

15. A robotic surgical device comprising:

(a) an elongate body sized to be disposable through an incision in a patient, the elongate body comprising:
  (i) a first shoulder drivetrain disposed within the elongate body, the first shoulder drivetrain comprising:
    (A) a first motor;
    (B) a first driveshaft rotatably coupled to the first motor; and
    (C) a second motor disposed substantially coaxially with the first motor;
  (ii) a second shoulder drivetrain disposed within the elongate body, the second shoulder drivetrain comprising:
    (A) a third motor;
    (B) a second driveshaft rotatably coupled to the third motor; and
    (C) a fourth motor disposed substantially coaxially with the third motor;

(b) a first shoulder joint moveably coupled to a distal end of the elongate body, the first shoulder joint comprising:
  (i) a first upper gear rotatably coupled to the second motor;
  (ii) a first lower gear fixedly attached to the first driveshaft; and
  (iii) a first output gear mechanically engaged with first upper gear and the first lower gear;

(c) a second shoulder joint moveably coupled to the distal end of the elongate body, the second shoulder joint comprising:
  (i) a second upper gear rotatably coupled to the fourth motor;
  (ii) a second lower gear fixedly attached to the second driveshaft; and
  (iii) a second output gear mechanically engaged with second upper gear and the second lower gear;

(d) a first arm operably coupled to the first shoulder joint; and (e) a second arm operably coupled to the second shoulder joint.

16. The robotic device of claim 15, wherein the second motor is distal to the first motor;

the fourth motor is distal to the third motor;

the first output gear has an axis of rotation that is transverse to an axis of rotation of the first upper gear and the first lower gear; and the second output gear has an axis of rotation that is transverse to an axis of rotation of the second upper gear and the second lower gear.

17. The robotic device of claim 15, wherein the first arm is a first upper arm, wherein the device further comprises a first forearm operably coupled to the first upper arm, and wherein the second arm is a second upper arm, wherein the device further comprises a second forearm operably coupled to the second upper arm.

18. The robotic device of claim 17, further comprising:
(a) a first end effector operably coupled to the first forearm; and
(b) a second end effector operably coupled to the second forearm.

19. The robotic device of claim 15, wherein the second motor is disposed distal of the first motor within the elongate device body.

* * * * *